United States Patent [19]
Schumm et al.

[11] Patent Number: 5,843,660
[45] Date of Patent: Dec. 1, 1998

[54] MULTIPLEX AMPLIFICATION OF SHORT TANDEM REPEAT LOCI

[75] Inventors: James W. Schumm, Madison; Katherine A. Micka, Oregon; Dawn R. Rabbach, DeForest, all of Wis.

[73] Assignee: Promega Corporation, Madison, Wis.

[21] Appl. No.: 632,575

[22] Filed: Apr. 15, 1996

Related U.S. Application Data

[63] Continuation-in-part of Ser. No. 316,544, Sep. 30, 1994.

[51] Int. Cl.$^6$ .............................. C12Q 1/68; C12P 19/34; C07H 21/04
[52] U.S. Cl. ........................ 435/6; 435/91.2; 536/24.33; 935/77; 935/78
[58] Field of Search .................................. 435/5, 6, 91.1, 435/91.2; 536/23.1, 24.3, 24.33

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 5,192,659 | 3/1993 | Simons . |
| 5,364,759 | 11/1994 | Caskey et al. . |
| 5,422,252 | 6/1995 | Walker et al. . |
| 5,599,666 | 2/1997 | Schumm et al. ............................ 435/6 |

FOREIGN PATENT DOCUMENTS

| | | |
|---|---|---|
| WO 93/18177 | 9/1993 | WIPO . |
| WO 93/18178 | 9/1993 | WIPO . |

OTHER PUBLICATIONS

Lin et al. (1996) Proc. Natl. Acad. Sci. USA 93:2582–7.
Gill (1995) Electrophoresis 16:1543–52.
Oetting (1995) Genomics 30:450–8.
Oldroyd (1995) Electrophoresis 16:334–7.
Lins et al. (1996) BioTechniques 20:882–889.
Kimpton et al. (1996) Electrophoresis 17:1283–93.
Budowle (1995) J. Forensic Sci. 40:45–54.
McKeown et al. (1995) Nucleic Acids Res. 23:2337–8.
Kimpton (1994) Adv. Forensic Haemogenet 5:309–11.
Castro (1996) Adv. Forensic Haemogenet 6:266–8.
Kimpton (1994) Int J. Legal Med. 106:302–11.
Alford et al. (1994) Am. J. Hum. Genet. 55:190–95.
Tully (1993) Human Genet. 92:554–62.
Micka et al. (1996) J. Forensic Sci. 41:582–90.
Wildenberg et al. (1995) Am. J. Hum. Genet. 57:755–65.
Hecht et al. (1993) Genomics 18:661–666.
Urquhart et al. (1994) Int. J. Legal Med. 107:13–20.
Andersen (1996) Forensic Sci Int. 78:47–64.
Furedi (1996) Int. J. Legal Medicine 109:100–101.
Rousselet (1996) Int. J. Legal Medicine 109:5–9.
Robertson (1995) Electrophoresis 16:156–76.
Rousselet (1996) Adv. Forensic Haemogenet 6:139–141.
Fuentes et al. (1993) Int. J. Legeal Medicine 105:271–77.
De Stefano (1996) Int J. Legal Med. 108:256–8.
GenBank Accession Numbers: G08343; G08745; G08051; G07948; G07948; and L16393.

Adamson, D., et al. (1995) "A Collection of Ordered Tetranucleotide–Repeat Markers from the Human Genome," *Am. J. Hum. Genet*. 57: 619–628.
Murray, J. C., et al. (1994) "A Comprehensive Human Linkage Map with Centimorgan Density," *Science* 265: 2049–2054.
Hudson, T. J., et al. (1992) "Isolation and Chromosomal Assignment of 100 Highly Informative Human Simple Sequence Repeat Polymorphisms," *Genomics* 13: 622–629.
Edwards et al. (1991) "DNA Typing and Genetic Mapping with Trimeric and Tetrameric Tandem Repeats," *Am. J. Hum. Genet*. 49: 746–756.
Beckman, J. S., et al. (1992) "Survey of Human and Rat Microsatellites," *Genomics* 12: 627–631.
Nakamura, Y., et al. (1987) "Variable Numbers of Tandem Repeat (VNTR) Markers for Human Gene Mapping," *Science* 235: 1616–1622.
Jeffreys, A. J., et al. (1985) "Hypervariable 'minisatellite'regions in human DNA," *Nature* 314:67–73.
Litt, M. and Luty, J. A. (1989) "A Hypervariable Microsatellite Revealed by In Vitro Amplification of a Dinucleotide Repeat within the Cardiac Muscle Actin Gene," *Am. J. Hum. Genet*. 44: 397–401.
Tautz, D., et al. (1986) "Cryptic simplicity in DNA is a major source of genetic variation," *Nature* 322: 652–656.
Weber, J. L., et al. (1989) "Abundant Class of Human DNA Polymorphisms Which Can Be Typed Using the Polymerase Chain Reaction," *Am. J. Hum. Genet*. 44: 388–396.
Chamberlain, J. S., et al. (1988) "Deletion screening of the Duchenne muscular dystrophy locus via multiplex DNA amplification," *Nucleic Acid Res*. 16: 11141–11156.
Chamberlain, J. S., et al. (1989), "Multiplex PCR for the Diagnosis of Duchenne Muscular Dystrophy,"in *PCR Protocols, A Guide to Methods and Application* (ed. Gelfand, D. H., et al.) pp. 272–281.
Beggs, A. H., et al. (1990) "Detection of 98% DMD/BMD gene deletions by polymerase chain reaction," *Hum. Genet*. 86: 45–48.
Clemens, P. R., et al. (1991). "Carrier Detection and Prenatal Diagnosis in Duchenne and Becker Muscular Dystrophy Families, Using Dinucleotide Repeat Polymorphisms," *Am J. Hum. Genet*. 49:951–960.
Schwartz, J. S., et al. (1992) "Fluorescent Multiplex Linkage Analysis and Carrier Detection for Duchenne/Becker Muscular Dystrophy," *Am J. Hum. Genet*. 51: 721–729.
Covone, A. E., et al. (1992) "Screening Duchenne and Becker Muscular Dystrophy Patients for Deletions in 30 Exons of the Dystrophin Gene by Three–Multiplex PCR," *Am. J. Hum. Genet*. 51:675–677.
Gibbs, R. A. et al. (1990) "Multiplex DNA Deletion Detection and Exon Sequencing of the Hypoxanthine Phosphoribosyltransferase Gene in Lesch–Nyhan Families," *Genomics* 7: 235–244.

(List continued on next page.)

*Primary Examiner*—Stephanie W. Zitomer
*Attorney, Agent, or Firm*—Grady J. Frenchick; Stroud, Stroud, Willink, Thompson & Howard; Karen B. King

[57] ABSTRACT

The present invention is directed to the simultaneous amplification of multiple distinct genetic loci using PCR or other amplification systems to determine in one reaction the alleles of each of the loci contained within the multiplex.

43 Claims, 19 Drawing Sheets

OTHER PUBLICATIONS

Estivill, X., et al. (1991) "Prenatal diagnosis of cystic fibrosis by multiplex PCR of mutation and microsatellite alleles," *Lancet*338: 458.

Fortina, P., et al. (1992) "Non–radioactive detection of the most common mutation in the cystic fibrosis transmembrane conductance regulator gene by multiplex allele–specific polymerase chain reaction," *Hum. Genet.*90: 375–378.

Ferrie, R. M., et al. (1992) "Development, Multiplexing, and Application of ARMS Tests for Common Mutations in the CFTR Gene," *Am. J. Hum. Genet.*51: 251–262.

Morral, N., et al. (1992) "Multiplex PCR Amplification of Three Microsatellites within the CFTR Gene," *Genomics*51: 1362–1364.

Lohmann, D., et al. (1992) "Detection of small RB1 gene deletions in retinoblastoma by multiplex PCR and high–resolution gel electrophoresis," *Hum. Genet.*89: 49–53.

Huang, T. H.–M., et al. (1992) "Genetic Mapping of Four Dinucleotide Repeat Loci, DXS453, DXS458, DXS454, and DXS424, on the X Chromosome Using Multiplex Polymerase Chain Reaction," *Genomics*13: 375–380.

Edwards, A., et al. (1992) "Genetic Variation at Five Trimeric and Tetrameric Tandem Repeat Loci in Four Human Population Groups," *Genomics*12:241–253.

Kimpton, C. P., et al. (1993) "Automated DNA Profiling Employing Multiplex Amplification of Short Tandem Repeat Loci," *PCR Methods and Applications*3: 13–22.

Hammond, H. A., et al. (1994) "Evaluation of 13 Short Tandem Repeat Loci for Use in Personal Identification Application," *Am. J. Hum. Genet.*55: 175–189.

Oldroyd, N. J., et al. (1995) "A Highly Discriminating Octoplex Short Tandem Repeat Polymerase Chain Reaction System Suitable for Human Individual Identification," *Electrophoresis*16: 334–337.

Ballabio, A., et al. (1991) "PCR test for cystic fibrosis deletion," *Nature*, 343: 220.

Presley, L. A., et al. (1993) "The Implementation of the Polymerase Chain Reaction (PCR) HLA DQ Alpha Typing by the FBI Laboratory,"in The Third International Symposium on Human Identification 1992, pp. 245–269.

Bever, R. A., et al. (1992) "Characterization of Five VNTR Loci by Hae III RFLP Analysis: Application to Paternity Testing,"in The Second International Symposium on Human Identification 1991, pp. 103–128.

Botstein, D., et al. (1980) "Construction of a Genetic Linkage Map in Man Using Restriction Fragment Length Polymorphisms," *Am. J. Hum. Genet.*32: 314–331.

Patel, P. I., et al. (1984) "Organization of the HPRT Gene and Related Sequences in the Human Genome," *Somat Cell Mol Genet*10: 483–493.

Gill, P., et al. (1985) "Forensic application of DNA 'fingerprints'," *Nature*318: 577–579.

Brunk C. F., et al. 4 (1979) "Assay for Nanogram Quantities of DNA in Cellular Homogenates," *Anal Biochem*92: 497–500.

Waye, J. S., et al. (1989) "A Simple and Sensitive Method for Quantifying Human Genomic DNA in Forensic Specimen Extracts," *Bio Techniques*vol. 7 No. 8, pp. 852–855.

Waye, J. S., et al. (1991) "Sensitive and Specific Quantification of Human Genomic Deoxyribonucleic Acid (DNA) in Forensic Science Specimens: Casework Examples," *J. Forensic Sci.*, 36:1198–1203.

Saiki, R. K., et al. (1985) "Enzymatic Amplification of β–Globin Genomic Sequences and Restriction Site Analysis for Diagnosis of Sickle Cell Anemia," *Science*230: 1350–1354.

Kwoh, D. Y., et al. (1990) "Target amplification systems in nucleic acid–based diagnostic approaches," *American Biotechnology Laboratory*, Oct. 1990.

Walker, G. T., et al. (1992) "Isothermal in vitro amplification of DNA by a restriction enzyme/DNA polymerase system," *Proc. Natl. Acad. Sci., U.S.A.*89:392–396.

Sambrook, J., et al. (1989) In *Molecular Cloning—A Laboratory Manual*, 2nd edition, Cold Spring Harbor Laboratory Press, pp. 13.45–13.57.

Bassam, B. J., et al. (1991) "Fast and Sensitive Silver Staining of DNA in Polyacrylamide Gels," *Anal. Biochem.*196: 80–83.

Puers, C., et al. (1993) "Identification of Repeat Sequence Heterogeneity at the Polymorphic Short Tandem Repeat Locus HUMTHO1[AATG]$_n$,and Reassignment of Alleles in Population Analysis by Using a Locus–specific Allelic Ladder," *Am. J. Hum. Genet.* 53:953–958.

Kobayashi, Y. (1988) "A Method to Cast Thin Sequencing Gels," *BRL Focus*10: 73–74.

Edwards, M. C., et al. (1994) "Multiplex PCR: Advantages, Development, and Applications," *PCR Methods and Applications*3: S65–S75.

Alford, R. L., et al. (1994) "Rapid and Efficient Resolution of Parentage by Amplification of Short Tandem Repeats," *Am. J. Hum. Genet.* 55:190–195.

Chakraborty, R. (1993) "A Class of Population Genetic Questions Formulated as the Generalized Occupancy Problem," *Genetics*, vol. 134, pp. 953–958.

Fregeau, C. J., et al. (1993) "DNA Typing with Fluorescently Tagged Short Tandem Repeats: A Sensitive and Accurate Approach to Human Identification," *BioTechniques*, vol. 15, No. 1, pp. 100–119.

Schumm et al., "Development of Nonisotopic Multiplex Amplification Sets for Analysis of Polymorphic STR Loci," *Fourth International Symposium on Human Identification*1993, pp. 177–187.

SEQUENCE LISTING ( 1 ) GENERAL INFORMATION:

( i i i ) NUMBER OF SEQUENCES: 61

( 2 ) INFORMATION FOR SEQ ID NO:1:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: Human Genomic DNA ( i i i ) HYPOTHETICAL: no ( v i i i ) POSITION IN GENOME:
        ( B ) MAP POSITION: D7S820

( x i ) SEQUENCE DESCRIPTION: SEQ ID NO:1:

```
            GAACACTTGT CATAGTTTAG AACG                    24
```

( 2 ) INFORMATION FOR SEQ ID NO:2:

( i ) SEQUENCE CHARACTERISTICS:
        ( A ) LENGTH: 23
        ( B ) TYPE: Nucleic Acid
        ( C ) STRANDEDNESS: Single
        ( D ) TOPOLOGY: Linear ( v i i i ) POSITION IN GENOME:
        ( B ) MAP POSITION: D7S820

( x i ) SEQUENCE DESCRIPTION: SEQ ID NO:2:

```
            CTGAGGTATC AAAAACTCAG AGG                     23
```

( 2 ) INFORMATION FOR SEQ ID NO:3:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( v i i i ) POSITION IN GENOME:
        ( B ) MAP POSITION: D13S317

( x i ) SEQUENCE DESCRIPTION: SEQ ID NO:3:

```
              ACAGAAGTCT GGGATGTGGA                       20
```

( 2 ) INFORMATION FOR SEQ ID NO:4:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( v i i i ) POSITION IN GENOME:
        ( B ) MAP POSITION: D13S317

( x i ) SEQUENCE DESCRIPTION: SEQ ID NO:4:

```
              GCCCAAAAAG ACAGACAGAA                       20
```

( 2 ) INFORMATION FOR SEQ ID NO:5:

( i ) SEQUENCE CHARACTERISTICS:
        ( A ) LENGTH: 20

(B) TYPE: Nucleic Acid
(C) STRANDEDNESS: Single
(D) TOPOLOGY: Linear (viii) POSITION IN GENOME:
(B) MAP POSITION: D5S818

(xi) SEQUENCE DESCRIPTION: SEQ ID NO:5:

GGGTGATTTT CCTCTTTGGT 20

(2) INFORMATION FOR SEQ ID NO:6:

(i) SEQUENCE CHARACTERISTICS:
(A) LENGTH: 20
(B) TYPE: Nucleic Acid
(C) STRANDEDNESS: Single
(D) TOPOLOGY: Linear (viii) POSITION IN GENOME:
(B) MAP POSITION: D5S818

(xi) SEQUENCE DESCRIPTION: SEQ ID NO:6:

TGATTCCAAT CATAGCCACA 20

(2) INFORMATION FOR SEQ ID NO:7:

(i) SEQUENCE CHARACTERISTICS:
(A) LENGTH: 26
(B) TYPE: Nucleic Acid
(C) STRANDEDNESS: Single
(D) TOPOLOGY: Linear (viii) POSITION IN GENOME:
(B) MAP POSITION: D3S1539

(xi) SEQUENCE DESCRIPTION: SEQ ID NO:7:

TCTCTTTCCA TTACTCTCTC CATAGC 26

(2) INFORMATION FOR SEQ ID NO:8:

(i) SEQUENCE CHARACTERISTICS:
(A) LENGTH: 22
(B) TYPE: Nucleic Acid
(C) STRANDEDNESS: Single
(D) TOPOLOGY: Linear (viii) POSITION IN GENOME:
(B) MAP POSITION: D3S1539

(xi) SEQUENCE DESCRIPTION: SEQ ID NO:8:

AGTGCTGTTT TAGCTTCCAG GA 22

(2) INFORMATION FOR SEQ ID NO:9:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: D17S1298

(xi) SEQUENCE DESCRIPTION: SEQ ID NO:9:

GTAGGTCTTT TGGTTGCCAG TATG 24

(2) INFORMATION FOR SEQ ID NO:10:

(i) SEQUENCE CHARACTERISTICS:
(A) LENGTH: 24

(B) TYPE: Nucleic Acid
(C) STRANDEDNESS: Single
(D) TOPOLOGY: Linear (viii) POSITION IN GENOME:
(B) MAP POSITION: D17S1298

(xi) SEQUENCE DESCRIPTION: SEQ ID NO:10:

TGTCAGTAAA CCTGTGACCT GAGT 24

(2) INFORMATION FOR SEQ ID NO:11:

(i) SEQUENCE CHARACTERISTICS:
(A) LENGTH: 26
(B) TYPE: Nucleic Acid
(C) STRANDEDNESS: Single
(D) TOPOLOGY: Linear (viii) POSITION IN GENOME:
(B) MAP POSITION: D20S481

(xi) SEQUENCE DESCRIPTION: SEQ ID NO:11:

AATGGTGAGA AATGGGTTAT GAGTGC 26

(2) INFORMATION FOR SEQ ID NO:12:

(i) SEQUENCE CHARACTERISTICS:
(A) LENGTH: 25
(B) TYPE: Nucleic Acid
(C) STRANDEDNESS: Single
(D) TOPOLOGY: Linear (viii) POSITION IN GENOME:
(B) MAP POSITION: D20S481

(xi) SEQUENCE DESCRIPTION: SEQ ID NO:12:

TTTCCGGCTT TGTGTCATAA AACAG 25

(2) INFORMATION FOR SEQ ID NO:13:

(i) SEQUENCE CHARACTERISTICS:
(A) LENGTH: 20
(B) TYPE: Nucleic Acid
(C) STRANDEDNESS: Single
(D) TOPOLOGY: Linear (viii) POSITION IN GENOME:
(B) MAP POSITION: D9S930

(xi) SEQUENCE DESCRIPTION: SEQ ID NO:13:

TGGACAACAG AGTGAGATGC 20

(2) INFORMATION FOR SEQ ID NO:14:

(i) SEQUENCE CHARACTERISTICS:
(A) LENGTH: 23
(B) TYPE: Nucleic Acid
(C) STRANDEDNESS: Single
(D) TOPOLOGY: Linear (viii) POSITION IN GENOME:
(B) MAP POSITION: D9S930

(xi) SEQUENCE DESCRIPTION: SEQ ID NO:14:

GCTATGGGAA TTACAAGCAG GAA 23

(2) INFORMATION FOR SEQ ID NO:15:

(i) SEQUENCE CHARACTERISTICS:
(A) LENGTH: 26

( B ) TYPE: Nucleic Acid
              ( C ) STRANDEDNESS: Single
              ( D ) TOPOLOGY: Linear ( v i i i ) POSITION IN GENOME:
              ( B ) MAP POSITION: D10S1239

( x i ) SEQUENCE DESCRIPTION: SEQ ID NO:15:

CTTTGAAATG GACCCCTAGC TAATGT                                                            2 6

( 2 ) INFORMATION FOR SEQ ID NO:16:

( i ) SEQUENCE CHARACTERISTICS:
              ( A ) LENGTH: 21
              ( B ) TYPE: Nucleic Acid
              ( C ) STRANDEDNESS: Single
              ( D ) TOPOLOGY: Linear ( v i i i ) POSITION IN GENOME:
              ( B ) MAP POSITION: D10S1239

( x i ) SEQUENCE DESCRIPTION: SEQ ID NO:16:

CACCCTGTCC CCAGCTATCT G                                                                 2 1

( 2 ) INFORMATION FOR SEQ ID NO:17:

( i ) SEQUENCE CHARACTERISTICS:
              ( A ) LENGTH: 19
              ( B ) TYPE: Nucleic Acid
              ( C ) STRANDEDNESS: Single
              ( D ) TOPOLOGY: Linear ( v i i i ) POSITION IN GENOME:
              ( B ) MAP POSITION: D14S118

( x i ) SEQUENCE DESCRIPTION: SEQ ID NO:17:

CAGCTTGGGC AACATAGGG                                                                    1 9

( 2 ) INFORMATION FOR SEQ ID NO:18:

( i ) SEQUENCE CHARACTERISTICS:
              ( A ) LENGTH: 24
              ( B ) TYPE: Nucleic Acid
              ( C ) STRANDEDNESS: Single
              ( D ) TOPOLOGY: Linear ( v i i i ) POSITION IN GENOME:
              ( B ) MAP POSITION: D14S118

( x i ) SEQUENCE DESCRIPTION: SEQ ID NO:18:

CAAACTCCTG AGGTCAAACA ATCC                                                              2 4

( 2 ) INFORMATION FOR SEQ ID NO:19:

( i ) SEQUENCE CHARACTERISTICS:
              ( A ) LENGTH: 21
              ( B ) TYPE: Nucleic Acid
              ( C ) STRANDEDNESS: Single
              ( D ) TOPOLOGY: Linear ( v i i i ) POSITION IN GENOME:
              ( B ) MAP POSITION: D14S562

( x i ) SEQUENCE DESCRIPTION: SEQ ID NO:19:

CTTGGAGGGT GGGGTGGCTA A                                                                 2 1

( 2 ) INFORMATION FOR SEQ ID NO:20:

( i ) SEQUENCE CHARACTERISTICS:
              ( A ) LENGTH: 24

( B ) TYPE: Nucleic Acid
( C ) STRANDEDNESS: Single
( D ) TOPOLOGY: Linear ( v i i i ) POSITION IN GENOME:
( B ) MAP POSITION: D14S562

( x i ) SEQUENCE DESCRIPTION: SEQ ID NO:20:

CGAAATTTTG TTGCCTTGCT CTGG 24

( 2 ) INFORMATION FOR SEQ ID NO:21:

( i ) SEQUENCE CHARACTERISTICS:
( A ) LENGTH: 21
( B ) TYPE: Nucleic Acid
( C ) STRANDEDNESS: Single
( D ) TOPOLOGY: Linear ( v i i i ) POSITION IN GENOME:
( B ) MAP POSITION: D14S548

( x i ) SEQUENCE DESCRIPTION: SEQ ID NO:21:

CCTGGGCAAC AGAGTGAGAC T 21

( 2 ) INFORMATION FOR SEQ ID NO:22:

( i ) SEQUENCE CHARACTERISTICS:
( A ) LENGTH: 24
( B ) TYPE: Nucleic Acid
( C ) STRANDEDNESS: Single
( D ) TOPOLOGY: Linear ( v i i i ) POSITION IN GENOME:
( B ) MAP POSITION: D14S548

( x i ) SEQUENCE DESCRIPTION: SEQ ID NO:22:

ACCCAGCTTT AACAGTTTGT GCTT 24

( 2 ) INFORMATION FOR SEQ ID NO:23:

( i ) SEQUENCE CHARACTERISTICS:
( A ) LENGTH: 23
( B ) TYPE: Nucleic Acid
( C ) STRANDEDNESS: Single
( D ) TOPOLOGY: Linear ( v i i i ) POSITION IN GENOME:
( B ) MAP POSITION: D16S490

( x i ) SEQUENCE DESCRIPTION: SEQ ID NO:23:

GGGCGGACAC AGAATGTAAA ATC 23

( 2 ) INFORMATION FOR SEQ ID NO:24:

( i ) SEQUENCE CHARACTERISTICS:
( A ) LENGTH: 24
( B ) TYPE: Nucleic Acid
( C ) STRANDEDNESS: Single
( D ) TOPOLOGY: Linear ( v i i i ) POSITION IN GENOME:
( B ) MAP POSITION: D16S490

( x i ) SEQUENCE DESCRIPTION: SEQ ID NO:24:

AAACCCAAAT AGATGACAGG CACA 24

( 2 ) INFORMATION FOR SEQ ID NO:25:

( i ) SEQUENCE CHARACTERISTICS:
( A ) LENGTH: 24

( B ) TYPE: Nucleic Acid
                ( C ) STRANDEDNESS: Single
                ( D ) TOPOLOGY: Linear ( v i i i ) POSITION IN GENOME:
                ( B ) MAP POSITION: D16S753

( x i ) SEQUENCE DESCRIPTION: SEQ ID NO:25:

GCACTCCAGG CTGAATGACA GAAC                                    2 4

( 2 ) INFORMATION FOR SEQ ID NO:26:

( i ) SEQUENCE CHARACTERISTICS:
                ( A ) LENGTH: 24
                ( B ) TYPE: Nucleic Acid
                ( C ) STRANDEDNESS: Single
                ( D ) TOPOLOGY: Linear ( v i i i ) POSITION IN GENOME:
                ( B ) MAP POSITION: D16S753

( x i ) SEQUENCE DESCRIPTION: SEQ ID NO:26:

GCAGTGCCGC CTATTTTTGT GAAT                                    2 4

( 2 ) INFORMATION FOR SEQ ID NO:27:

( i ) SEQUENCE CHARACTERISTICS:
                ( A ) LENGTH: 24
                ( B ) TYPE: Nucleic Acid
                ( C ) STRANDEDNESS: Single
                ( D ) TOPOLOGY: Linear ( v i i i ) POSITION IN GENOME:
                ( B ) MAP POSITION: D17S1299

( x i ) SEQUENCE DESCRIPTION: SEQ ID NO:27:

ACCCTGATGA GATAGCACTT GAGC                                    2 4

( 2 ) INFORMATION FOR SEQ ID NO:28:

( i ) SEQUENCE CHARACTERISTICS:
                ( A ) LENGTH: 24
                ( B ) TYPE: Nucleic Acid
                ( C ) STRANDEDNESS: Single
                ( D ) TOPOLOGY: Linear ( v i i i ) POSITION IN GENOME:
                ( B ) MAP POSITION: D17S1299

( x i ) SEQUENCE DESCRIPTION: SEQ ID NO:28:

CACTGTGTGG AGGTGTAGCA GAGA                                    2 4

( 2 ) INFORMATION FOR SEQ ID NO:29:

( i ) SEQUENCE CHARACTERISTICS:
                ( A ) LENGTH: 24
                ( B ) TYPE: Nucleic Acid
                ( C ) STRANDEDNESS: Single
                ( D ) TOPOLOGY: Linear ( v i i i ) POSITION IN GENOME:
                ( B ) MAP POSITION: D16S539

( x i ) SEQUENCE DESCRIPTION: SEQ ID NO:29:

GGGGGTCTAA GAGCTTGTAA AAAG                                    2 4

( 2 ) INFORMATION FOR SEQ ID NO:30:

( i ) SEQUENCE CHARACTERISTICS:
                ( A ) LENGTH: 26

( B ) TYPE: Nucleic Acid
( C ) STRANDEDNESS: Single
( D ) TOPOLOGY: Linear ( v i i i ) POSITION IN GENOME:
( B ) MAP POSITION: D16S539

( x i ) SEQUENCE DESCRIPTION: SEQ ID NO:30:

TGTGCATCTG TAAGCATGTA TCTATC     26

( 2 ) INFORMATION FOR SEQ ID NO:31:

( i ) SEQUENCE CHARACTERISTICS:
( A ) LENGTH: 23
( B ) TYPE: Nucleic Acid
( C ) STRANDEDNESS: Single
( D ) TOPOLOGY: Linear ( v i i i ) POSITION IN GENOME:
( B ) MAP POSITION: D22S683

( x i ) SEQUENCE DESCRIPTION: SEQ ID NO:31:

CGAAGGTTGC ATTGAGCCAA GAT     23

( 2 ) INFORMATION FOR SEQ ID NO:32:

( i ) SEQUENCE CHARACTERISTICS:
( A ) LENGTH: 24
( B ) TYPE: Nucleic Acid
( C ) STRANDEDNESS: Single
( D ) TOPOLOGY: Linear ( v i i i ) POSITION IN GENOME:
( B ) MAP POSITION: D22S683

( x i ) SEQUENCE DESCRIPTION: SEQ ID NO:32:

TGGTGGAAAT GCCTCATGTA GAAA     24

( 2 ) INFORMATION FOR SEQ ID NO:33:

( i ) SEQUENCE CHARACTERISTICS:
( A ) LENGTH: 24
( B ) TYPE: Nucleic Acid
( C ) STRANDEDNESS: Single
( D ) TOPOLOGY: Linear ( v i i i ) POSITION IN GENOME:
( B ) MAP POSITION: HUMCSF1PO ( x i ) SEQUENCE DESCRIPTION: SEQ ID NO:33:

AACCTGAGTC TGCCAAGGAC TAGC     24

( 2 ) INFORMATION FOR SEQ ID NO:34:

( i ) SEQUENCE CHARACTERISTICS:
( A ) LENGTH: 24
( B ) TYPE: Nucleic Acid
( C ) STRANDEDNESS: Single
( D ) TOPOLOGY: Linear ( v i i i ) POSITION IN GENOME:
( B ) MAP POSITION: HUMCSF1PO ( x i ) SEQUENCE DESCRIPTION: SEQ ID NO:34:

TTCCACACAC CACTGGCCAT CTTC     24

( 2 ) INFORMATION FOR SEQ ID NO:35:

( i ) SEQUENCE CHARACTERISTICS:
( A ) LENGTH: 24

(B) TYPE: Nucleic Acid
(C) STRANDEDNESS: Single
(D) TOPOLOGY: Linear (viii) POSITION IN GENOME:
(B) MAP POSITION: HUMTPOX (xi) SEQUENCE DESCRIPTION: SEQ ID NO:35:

ACTGGCACAG AACAGGCACT TAGG 24

(2) INFORMATION FOR SEQ ID NO:36:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: HUMTPOX (xi) SEQUENCE DESCRIPTION: SEQ ID NO:36:

GGAGGAACTG GGAACCACAC AGGT 24

(2) INFORMATION FOR SEQ ID NO:37:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: HUMTHO1

(xi) SEQUENCE DESCRIPTION: SEQ ID NO:37:

ATTCAAAGGG TATCTGGGCT CTGG 24

(2) INFORMATION FOR SEQ ID NO:38:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: HUMTHO1

(xi) SEQUENCE DESCRIPTION: SEQ ID NO:38:

GTGGGCTGAA AAGCTCCCGA TTAT 24

(2) INFORMATION FOR SEQ ID NO:39:

(i) SEQUENCE CHARACTERISTICS:
(A) LENGTH: 29
(B) TYPE: Nucleic Acid
(C) STRANDEDNESS: Single
(D) TOPOLOGY: Linear (viii) POSITION IN GENOME:
(B) MAP POSITION: HUMvWFA31

(xi) SEQUENCE DESCRIPTION: SEQ ID NO:39:

GAAAGCCCTA GTGGATGATA AGAATAATC 29

(2) INFORMATION FOR SEQ ID NO:40:

(i) SEQUENCE CHARACTERISTICS:
(A) LENGTH: 30

(B) TYPE: Nucleic Acid
(C) STRANDEDNESS: Single
(D) TOPOLOGY: Linear (viii) POSITION IN GENOME:
(B) MAP POSITION: HUMvWFA31

(xi) SEQUENCE DESCRIPTION: SEQ ID NO:40:

GGACAGATGA TAAATACATA GGATGGATGG    30

(2) INFORMATION FOR SEQ ID NO:41:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: HUMF13A01

(xi) SEQUENCE DESCRIPTION: SEQ ID NO:41:

GAGGTTGCAC TCCAGCCTTT GCAA    24

(2) INFORMATION FOR SEQ ID NO:42:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: HUMF13A01

(xi) SEQUENCE DESCRIPTION: SEQ ID NO:42:

TTCCTGAATC ATCCCAGAGC CACA    24

(2) INFORMATION FOR SEQ ID NO:43:

(i) SEQUENCE CHARACTERISTICS:
(A) LENGTH: 23
(B) TYPE: Nucleic Acid
(C) STRANDEDNESS: Single
(D) TOPOLOGY: Linear (viii) POSITION IN GENOME:
(B) MAP POSITION: HUMFESFPS (xi) SEQUENCE DESCRIPTION: SEQ ID NO:43:

GCTGTTAATT CATGTAGGGA AGG    23

(2) INFORMATION FOR SEQ ID NO:44:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: HUMFESFPS (xi) SEQUENCE DESCRIPTION: SEQ ID NO:44:

GTAGTCCCAG CTACTTGGCT ACTC    24

(2) INFORMATION FOR SEQ ID NO:45:

(i) SEQUENCE CHARACTERISTICS:
(A) LENGTH: 20

(B) TYPE: Nucleic Acid
(C) STRANDEDNESS: Single
(D) TOPOLOGY: Linear (viii) POSITION IN GENOME:
(B) MAP POSITION: HUMBFXIII (xi) SEQUENCE DESCRIPTION: SEQ ID NO:45:

TGAGGTGGTG TACTACCATA                    20

(2) INFORMATION FOR SEQ ID NO:46:

(i) SEQUENCE CHARACTERISTICS:
(A) LENGTH: 20
(B) TYPE: Nucleic Acid
(C) STRANDEDNESS: Single
(D) TOPOLOGY: Linear (viii) POSITION IN GENOME:
(B) MAP POSITION: HUMBFXIII (xi) SEQUENCE DESCRIPTION: SEQ ID NO:46:

GATCATGCCA TTGCACTCTA                    20

(2) INFORMATION FOR SEQ ID NO:47:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: HUMLIPOL (xi) SEQUENCE DESCRIPTION: SEQ ID NO:47:

CTGACCAAGG ATAGTGGGAT ATAG               24

(2) INFORMATION FOR SEQ ID NO:48:

(i) SEQUENCE CHARACTERISTICS:
(A) LENGTH: 23
(B) TYPE: Nucleic Acid
(C) STRANDEDNESS: Single
(D) TOPOLOGY: Linear (viii) POSITION IN GENOME:
(B) MAP POSITION: HUMLIPOL (xi) SEQUENCE DESCRIPTION: SEQ ID NO:48:

GGTAACTGAG CGAGACTGTG TCT                23

(2) INFORMATION FOR SEQ ID NO:49:

(i) SEQUENCE CHARACTERISTICS:
(A) LENGTH: 18
(B) TYPE: Nucleic Acid
(C) STRANDEDNESS: Single
(D) TOPOLOGY: Linear (viii) POSITION IN GENOME:
(B) MAP POSITION: D3S1539

(xi) SEQUENCE DESCRIPTION: SEQ ID NO:49:

CCACCCTTTC AGCACCAG                      18

(2) INFORMATION FOR SEQ ID NO:50:

(i) SEQUENCE CHARACTERISTICS:
(A) LENGTH: 20
(B) TYPE: Nucleic Acid ( C ) STRANDEDNESS: Single
( D ) TOPOLOGY: Linear ( v i i i ) POSITION IN GENOME:
( B ) MAP POSITION: D19S253

( x i ) SEQUENCE DESCRIPTION: SEQ ID NO:50:

ATAGACAGAC AGACGGACTG 20

( 2 ) INFORMATION FOR SEQ ID NO:51:

( i ) SEQUENCE CHARACTERISTICS:
( A ) LENGTH: 19
( B ) TYPE: Nucleic Acid
( C ) STRANDEDNESS: Single
( D ) TOPOLOGY: Linear ( v i i i ) POSITION IN GENOME:
( B ) MAP POSITION: D19S253

( x i ) SEQUENCE DESCRIPTION: SEQ ID NO:51:

GGGAGTGGAG ATTACCCCT 19

( 2 ) INFORMATION FOR SEQ ID NO:52:

( i ) SEQUENCE CHARACTERISTICS:
( A ) LENGTH: 21
( B ) TYPE: Nucleic Acid
( C ) STRANDEDNESS: Single
( D ) TOPOLOGY: Linear ( v i i i ) POSITION IN GENOME:
( B ) MAP POSITION: D20S481

( x i ) SEQUENCE DESCRIPTION: SEQ ID NO:52:

AAAGCTCTCT GAAGCAGGTG T 21

( 2 ) INFORMATION FOR SEQ ID NO:53:

( i ) SEQUENCE CHARACTERISTICS:
( A ) LENGTH: 24
( B ) TYPE: Nucleic Acid
( C ) STRANDEDNESS: Single
( D ) TOPOLOGY: Linear ( v i i i ) POSITION IN GENOME:
( B ) MAP POSITION: D20S481

( x i ) SEQUENCE DESCRIPTION: SEQ ID NO:53:

CAGATTGCAC TAGAAAGAGA GGAA 24

( 2 ) INFORMATION FOR SEQ ID NO:54:

( i ) SEQUENCE CHARACTERISTICS:
( A ) LENGTH: 23
( B ) TYPE: Nucleic Acid
( C ) STRANDEDNESS: Single
( D ) TOPOLOGY: Linear ( v i i i ) POSITION IN GENOME:
( B ) MAP POSITION: D10S1239

( x i ) SEQUENCE DESCRIPTION: SEQ ID NO:54:

CACCCTGTCC CCAGCTATCT GGA 23

( 2 ) INFORMATION FOR SEQ ID NO:55:

( i ) SEQUENCE CHARACTERISTICS:
( A ) LENGTH: 27
( B ) TYPE: Nucleic Acid (C) STRANDEDNESS: Single
(D) TOPOLOGY: Linear (viii) POSITION IN GENOME:
(B) MAP POSITION: D9S930

(xi) SEQUENCE DESCRIPTION: SEQ ID NO:55:

AGTTGAATCT TGAGTCTCTC AGAGTCA 27

(2) INFORMATION FOR SEQ ID NO:56:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: D4S2368

(xi) SEQUENCE DESCRIPTION: SEQ ID NO:56:

TGTACTCATT TTCCCGCAAT GATG 24

(2) INFORMATION FOR SEQ ID NO:57:

(i) SEQUENCE CHARACTERISTICS:
(A) LENGTH: 24
(B) TYPE: Nucleic Acid
(C) STRANDEDNESS: Single
(D) TOPOLOGY: Linear (viii) POSITION IN GENOME:
(B) MAP POSITION: D4S2368

(xi) SEQUENCE DESCRIPTION: SEQ ID NO:57:

TCAGAAAGTA GGGTCTGGGC TCTT 24

(2) INFORMATION FOR SEQ ID NO:58:

(i) SEQUENCE CHARACTERISTICS:
(A) LENGTH: 28
(B) TYPE: Nucleic Acid
(C) STRANDEDNESS: Single
(D) TOPOLOGY: Linear (viii) POSITION IN GENOME:
(B) MAP POSITION: D16S539

(xi) SEQUENCE DESCRIPTION: SEQ ID NO:58:

TGTGCATCTG TAAGCATGTA TCTATCAT 28

(2) INFORMATION FOR SEQ ID NO:59:

(i) SEQUENCE CHARACTERISTICS:
(A) LENGTH: 32
(B) TYPE: Nucleic Acid
(C) STRANDEDNESS: Single
(D) TOPOLOGY: Linear (viii) POSITION IN GENOME:
(B) MAP POSITION: HUMvWFA31

(xi) SEQUENCE DESCRIPTION: SEQ ID NO:59:

GAAAGCCCTA GTGGATGATA AGAATAATCA GT 32

(2) INFORMATION FOR SEQ ID NO:60:

(i) SEQUENCE CHARACTERISTICS:
(A) LENGTH: 33
(B) TYPE: Nucleic Acid

```
        ( C ) STRANDEDNESS: Single
        ( D ) TOPOLOGY: Linear ( v i i i ) POSITION IN GENOME:
        ( B ) MAP POSITION: HUMvWFA31

( x i ) SEQUENCE DESCRIPTION: SEQ ID NO:60:

GGACAGATGA  TAAATACATA  GGATGGATGG  ATA                          3 3

( 2 ) INFORMATION FOR SEQ ID NO:61:

( i ) SEQUENCE CHARACTERISTICS:
        ( A ) LENGTH: 25
        ( B ) TYPE: Nucleic Acid
        ( C ) STRANDEDNESS: Single
        ( D ) TOPOLOGY: Linear ( v i i i ) POSITION IN GENOME:
        ( B ) MAP POSITION: D9S930

( x i ) SEQUENCE DESCRIPTION: SEQ ID NO:61:

GCTATGGGAA  TTACAAGCAG  GAAAC                                    2 5
```

MULTIPLEX AMPLIFICATION OF SHORT TANDEM REPEAT LOCI

This application is a continuation-in-part of U.S. patent application Ser. No. 08/316,544, filed Sep. 30, 1994. The entire disclosure of that parent application is incorporated by reference herein.

FIELD OF THE INVENTION

The present invention is generally directed to the detection of genetic markers in a genomic system. The present invention is more specifically directed to the simultaneous amplification of multiple distinct polymorphic genetic loci using the polymerase chain reaction or other amplification systems to determine in one reaction the alleles of each locus contained within the multiplex system.

BACKGROUND OF THE INVENTION

In recent years, the discovery and development of polymorphic short tandem repeats (STRs) as genetic markers has stimulated progress in the development of linkage maps, the identification and characterization of diseased genes, and the simplification and precision of DNA typing.

Many loci, at least in the human genome, contain polymorphic STR regions (Adamson, D., et al. (1995) "A collection of ordered tetranucleotide-repeat markers from the human genome," *Am. J. Hum. Genet.* 57: 619–628; Murray, J. C., et al. (1994) "A comprehensive human linkage map with centimorgan density," *Science* 265: 2049–2054; Hudson, T. J., Engelstein, M., Lee, M. K., Ho, E. C., Rubenfield, M. J., Adams, C. P., Housman, D. E., and Dracopoli, N. C. (1992) "Isolation and chromosomal assignment of 100 highly informative human simple sequence repeat polymorphisms," *Genomics* 13: 622–629). STR loci consist of short, repetitive sequence elements of 3 to 7 base pairs in length. It is estimated that there are 2,000,000 expected trimeric and tetrameric STRs present as frequently as once every 15 kilobases (kb) in the human genome (Edwards et al. (1991) "DNA typing and genetic mapping with trimeric and tetrameric tandem repeats." *Am. J. Hum. Genet.* 49: 746–756; Beckman, J. S., and Weber, J. L. (1992) "Survey of human and rat microsatellites," *Genomics* 12: 627–631). Nearly half of the STR loci studied by Edwards et al. (1991) are polymorphic, which provides a rich source of genetic markers.

Variation in the number of short tandem repeat units at a particular locus causes the length of the DNA at that locus to vary from allele to allele and from individual to individual. Such length polymorphism is reminiscent of variable number of tandem repeats (VNTR) loci (Nakamura, Y., et al. (1987) "Variable number of tandem repeat (VNTR) markers for human gene mapping," *Science* 235: 1616–1622) and minisatellite loci (Jeffreys, A. J., et al. (1985) "Hypervariable 'minisatellite' regions in human DNA," *Nature* 314: 67–73), both of which contain considerably longer repeat units than STR loci. Such length polymorphism is also reminiscent of the dinucleotide repeat form of microsatellite loci (Litt, M. and Luty, J. A. (1989) "A hypervariable microsatellite revealed by in-vitro amplification of a dinucleotide repeat within the cardiac muscle actin gene," *Am. J. Hum. Genet.* 44: 397–401, Tautz, D., et al. (1986) "Cryptic simplicity in DNA is a major source of genetic variation," *Nature* 322: 652–656, Weber, J. L. and May, P. E. (1989) "Abundant class of human DNA polymorphisms which can be typed using the polymerase chain reaction," *Am. J. Hum. Genet.* 44: 388–396; Beckmann and Weber, (1992)), a form of microsatellite loci with shorter repeat units than STR loci.

Polymorphic STR loci are extremely useful markers for human identification, paternity testing and genetic mapping. STR loci may be amplified via the polymerase chain reaction (PCR) by employing specific primer sequences identified in the regions flanking the tandem repeat.

Alleles of these loci are differentiated by the number of copies of the repeat sequence contained within the amplified region and are distinguished from one another following electrophoretic separation by any suitable detection method including radioactivity, fluorescence, silver stain, and color.

To minimize labor, materials and analysis time, it is desirable to analyze multiple loci and/or more samples simultaneously. One approach for reaching this goal involves amplification of multiple loci simultaneously in a single reaction. Such "multiplex" amplifications, as they are called, have been described extensively in the literature. Multiplex amplification sets have been extensively developed for analysis of genes related to human genetic diseases such as Duchenne Muscular Dystrophy (Chamberlain, J. S., et al. (1988) "Deletion screening of the Duchenne muscular dystrophy locus via multiplex DNA amplification," *Nucleic Acid Res.* 16: 11141–11156; Chamberlain, J. S., et al. (1989), "Multiple PCR for the diagnosis of Duchenne muscular dystrophy," In *PCR Protocols, A Guide to Methods and Application* (ed. Gelfand, D. H., et al.) pp. 272–281. Academic Press, San Diego, Calif.; Beggs, A. H., et al. (1990) "Detection of 98% DMD/BMD gene deletions by PCR," *Hum. Genet.* 86: 45–48; Clemens, P. R., et al. (1991). "Carrier detection and prenatal diagnosis in Duchenne and Becker muscular dystrophy families, using dinucleotide repeat polymorphisms," *Am J. Hum. Genet.* 49: 951–960; Schwartz, J. S., et al. (1992) "Fluorescent multiple linkage analysis and carrier detection for Duchenne/Becker's muscular dystrophy," *Am J. Hum. Genet.* 51: 721–729; Covone, A. E., et al. (1992) "Screening Duchenne and Becker muscular dystrophy patients for deletions in 30 exons of the dystrophin gene by three-multiplex PCR," *Am. J. Hum. Genet.* 51: 675–677), Lesch-Nyhan Syndrome (Gibbs, R. A., et al. (1990) "Multiple DNA deletion detection and exon sequencing of the hypoxanthine phosphoribosyltransferase gene in Lesch-Nyhan families," *Genomics* 7: 235–244), Cystic Fibrosis (Estivill, X., et al. (1991) "Prenatal diagnosis of cystic fibrosis by multiplex PCR of mutation and microsatellite alleles," *Lancet* 338: 458; Fortina, P., et al. (1992) "Non-radioactive detection of the most common mutations in the cystic fibrosis transmembrane conductance regulator gene by multiplex polymerase chain reaction," *Hum. Genet.* 90: 375–378; Ferrie, R. M., et al. (1992) "Development, multiplexing, and application of ARMS tests for common mutations in the CFTR gene," *Am. J. Hum. Genet.* 51: 251–262; Morral, N. and Estivill, X. (1992) "Multiplex PCR amplification of three microsatellites within the CFTR gene," *Genomics* 51: 1362–1364), and Retinoblasma (Lohmann, D., et al. (1992) "Detection of small RB1 gene deletions in retinoblastoma by multiplex PCR and high-resolution gel electrophoresis," *Hum. Genet.* 89: 49–53). Multiplex amplification of polymorphic microsatellite markers (Clemens et al. (1991); Schwartz et al. (1992); Huang, T. H.-M., et al. (1992) "Genetic mapping of four dinucleotide repeat loci DXS435, DXS45, DXS454, DXS424, on the X chromosome using the multiplex polymerase chain reaction," *Genomics* 13: 375–380) and even STR markers (Edwards, A., et al. (1992) "Genetic variation at five trimeric and tetrameric tandem repeat loci in four human population groups," *Genomics* 12: 241–253; Kimpton, C. P., et al.

(1993) "Automated DNA profiling employing multiplex amplification of short tandem repeat loci," *PCR Methods and Applications* 3: 13–22; Hammond, H. A., et al. (1994) "Evaluation of 13 STR loci for use in personal identification applications," *Am. J. Hum. Genet.* 55: 175–189; Schumm, J. W. et al. (1994) "Development of nonisotopic multiplex amplification sets for analysis of polymorphic STR loci," in "The Fourth International Symposium on Human Identification 1993," pp. 177–187; Oldroyd, N. J., et al. (1995) "A highly discriminating octoplex short tandem repeat polymerase chain reaction system suitable for human individual identification," *Electrophoresis* 16: 334–337) have been described.

These amplified products are generally separated by one of several methods of electrophoresis known to those skilled in the art. Several well-known methods of detection of the amplified products have also been described. While ethidium bromide staining or silver staining of amplified fragments is employed in some cases, in others it is preferred to use methods which label only one of the two strands of the amplified material. Examples of this include radioactive or fluorescent labeling of one of the two primers prior to the amplification of a locus. One of the more sophisticated approaches to detection is the use of different fluorescent labels to allow detection of amplified materials representing different loci, but existing in the same space following electrophoresis. The products of the different loci are differentiated with the use of filters or other discriminating detectors, which allow visualization of one fluorescent label at a time.

Reference is made to International Publications WO 93/18177 and WO 93/18178 to Fortina et al., which are directed to methods and kits for diagnosing diseases such as Cystic Fibrosis and β-thalassemia, respectively, using an allele-specific multiplex polymerase chain reaction system. According to Fortina et al., multiplex PCR has also been used for simultaneous amplification of multiple target sequences, permitting mutant allele scanning using two lanes of an agarose gel.

Ballabio, A. et al. (1991) "PCR Tests for Cystic Fibrosis Deletion," *Nature,* 343: 220, disclose a single-tube, multiplex allele-specific PCR test using two different dye-tagged fluorescent primers for detection of the F508 cystic fibrosis mutation.

While there are multiplex amplification procedures for specific loci, the use of multiplex amplification procedures is greatly desired for the detection of alleles in other types of loci such as specific STR loci. It is also desirable to identify primers which make multiplex amplification of such loci possible.

SUMMARY OF THE INVENTION

It is, therefore, an object of the present invention to provide a method and materials for the simultaneous amplification of multiple distinct polymorphic short tandem repeat (STR) loci using PCR or other amplification systems to determine, in one reaction, the alleles of each locus contained within the multiplex. Multiplex analysis of the sets of specific STR loci disclosed herein have not been previously described in the prior art. There has also not been any previous description of the sequences for many of the primers disclosed herein below, all of which are shown to be useful for multiplex amplification of such STR loci.

It is also an object of the present invention to provide a method, a kit, and primers specific for multiplex amplifications comprising specified loci.

These and other objects are addressed by the present invention which is directed to a method and materials for simultaneously analyzing or determining the alleles present at each individual locus of each multiplex. In general, the method of this invention comprises the steps of (a) obtaining at least one DNA sample to be analyzed, wherein the DNA sample has at least two loci which can be amplified together; (b) amplifying the STR sequences in the DNA sample; and (c) detecting the amplified materials in a fashion which reveals the polymorphic nature of the systems employed.

More specifically, the method of this invention is a method of simultaneously determining the alleles present in at least three tandem repeat loci from one or more DNA samples, such method comprising the steps of:

(a) obtaining at least one DNA sample to be analyzed, wherein the DNA sample has a set of at least three loci which can be amplified together, wherein the set of loci is selected from a specific group or sets of loci disclosed herein;

(b) co-amplifying the set of loci in a multiplex amplification reaction, wherein the product of the reaction is a mixture of amplified alleles from each of the co-amplified loci in the set; and (c) evaluating the amplified alleles in the mixture to determine the alleles present at each of the loci analyzed in the set within the DNA sample.

In one embodiment of this invention, three STR loci are amplified together, and the set of three co-amplified loci is selected from the group of sets consisting of:

D3S1539, D19S253, D13S317;

D10S1239, D9S930, D20S481;

D10S1239, D4S2368, D20S481;

D10S1239, D9S930, D4S2368;

D16S539, D7S820, D13S317; and

D10S1239, D9S930, D13S317.

In a more preferred embodiment of the method of this invention, the DNA sample has at least four STR loci which can be amplified together, and the set of co-amplified loci is selected from the group of loci consisting of:

D3S1539, D4S2368, D5S818, D7S820, D9S930, D10S1239,

D13S317, D14S118, D14S548, D14S562, D16S490, D16S539,

D16S753, D17S1298, D17S1299, D19S253, D20S481, D22S683,

HUMCSF1PO, HUMTPOX, HUMTH01, HUMFESFPS, HUMF13A01,

HUMBFXIII, HUMLIPOL, HUMvWFA31.

The set of at least four STR loci amplified together is more preferably a set selected from the sets of four loci comprising:

D3S1539, D7S820, D13S317, D5S818;

D17S1298, D7S820, D13S317, D5S818;

D20S481, D7S820, D13S317, D5S818;

D9S930, D7S820, D13S317, D5S818;

D10S1239, D7S820, D13S317, D5S818;

D14S118, D7S820, D13S317, D5S818;

D14S562, D7S820, D13S317, D5S818;

D14S548, D7S820, D13S317, D5S818;

D16S490, D7S820, D13S317, D5S818;

D17S1299, D7S820, D13S317, D5S818;

D16S539, D7S820, D13S317, D5S818;

D22S683, D7S820, D13S317, D5S818;
D16S753, D7S820, D13S317, D5S818;
D3S1539, D19S253, D13S317, D20S481;
D3S1539, D19S253, D4S2368, D20S481;
D10S1239, D9S930, D4S2368, D20S481; and
D16S539, D7S820, D13S317, HUMvWFA31.

More preferably, the set of STR loci amplified together is a set of six loci, selected from the sets of loci comprising:

D16S539, D7S820, D13S317, D5S818, HUMCSF1PO, HUMTPOX; and

D16S539, D7S820, D13S317, D5S818, HUMF13A01, HUMFESFPS.

Yet more preferably, the set of STR loci amplified together is a set of seven loci, selected from the sets of loci comprising:

D16S539, D7S820, D13S317, D5S818, HUMCSF1PO, HUMTPOX, HUMTH01; and

D16S539, D7S820, D13S317, D5S818, HUMF13A01, HUMFESFPS, HUMBFXIII.

Even more preferably, the set of STR loci amplified together is a set of eight loci, selected from the sets of loci comprising:

D16S539, D7S820, D13S317, D5S818, HUMCSF1PO, HUMTPOX, HUMTH01, HUMvWFA31; and

D16S539, D7S820, D13S317, D5S818, HUMF13A01, HUMFESFPS, HUMBFXIII, HUMLIPOL.

The multiplex amplification reaction step of the method is preferably done using a pair of primers flanking each locus in the set of loci co-amplified in the reaction. More preferably, pairs of primers are selected for the multiplex amplification reaction which produce alleles from each locus that do not overlap the alleles of the other loci in the set co-amplified therein, when the alleles are separated by gel electrophoresis. Even more preferably, the sequence of one of each pair of primers used in the multiplex amplification reaction is selected from a group of primer sequences consisting of:

SEQ ID NO:1 and SEQ ID NO:2, when one of the loci in the set is D7S820;

SEQ ID NO:3 and SEQ ID NO:4, when one of the loci in the set is D13S317;

SEQ ID NO:5 and SEQ ID NO:6, when one of the loci in the set is D5S818;

SEQ ID NO:7, SEQ ID NO:8, and SEQ ID NO:49, when one of the loci in the set is D3S1539;

SEQ ID NO:9, SEQ ID NO:10, when one of the loci in the set is D17S1298;

SEQ ID NO:11, SEQ ID NO:12, SEQ ID NO:52, SEQ ID NO:53, when one of the loci in the set is D20S481;

SEQ ID NO:13, SEQ ID NO:14, SEQ ID NO:55, SEQ ID NO:61, when one of the loci in the set is D9S930;

SEQ ID NO:15, SEQ ID NO:16, SEQ ID NO:54, when one of the loci in the set is D10S1239;

SEQ ID NO:17, SEQ ID NO:18, when one of the loci in the set is D14S118;

SEQ ID NO:19, SEQ ID NO:20, when one of the loci in the set is D14S562;

SEQ ID NO:21, SEQ ID NO:22, when one of the loci in the set is D14S548;

SEQ ID NO:23, SEQ ID NO:24, when one of the loci in the set is D16S490;

SEQ ID NO:25, SEQ ID NO:26, when one of the loci in the set is D16S753;

SEQ ID NO:27, SEQ ID NO:28, when one of the loci in the set is D17S1299;

SEQ ID NO:29, SEQ ID NO:30, SEQ ID NO:58, when one of the loci in the set is D16S539;

SEQ ID NO:31, SEQ ID NO:32, when one of the loci in the set is D22S683;

SEQ ID NO:33, SEQ ID NO:34, when one of the loci in the set is HUMCSF1PO;

SEQ ID NO:35, SEQ ID NO:36, when one of the loci in the set is HUMTPOX;

SEQ ID NO:37, SEQ ID NO:38, when one of the loci in the set is HUMTH01;

SEQ ID NO:39, SEQ ID NO:40, SEQ ID NO:59, SEQ ID NO:60 when one of the loci in the set is HUMvWFA31;

SEQ ID NO:41, SEQ ID NO:42, when one of the loci in the set is HUMF13A01;

SEQ ID NO:43, SEQ ID NO:44, when one of the loci in the set is HUMFESFPS;

SEQ ID NO:45, SEQ ID NO:46, when one of the loci in the set is HUMBFXIII;

SEQ ID NO:47, SEQ ID NO:48, when one of the loci in the set is HUMLIPOL;

SEQ ID NO:50, SEQ ID NO:51, when one of the loci in the set is D19S253; and

SEQ ID NO:56, SEQ ID NO:57, when one of the loci in the set is D4S2368.

In the method of this invention, the amplified alleles are preferably evaluated by comparing the amplified alleles to a size standard, wherein the size standard is selected from the group of size standards consisting of a DNA marker and a locus-specific allelic ladder. The evaluation of alleles is preferably done using polyacrylamide gel electrophoresis to separate the alleles, thereby forming a polyacrylamide gel of separated alleles. The separated alleles in the polyacrylamide gel are preferably determined by visualizing the alleles with an appropriate technique such as silver staining, but more preferably with fluorescent analysis.

Fluorescent analysis is preferably done by labeling one primer of each pair of primers used in the multiplex amplification reaction with a fluorescent label prior to use in the reaction. The fluorescent label used to label each such primer is preferably a fluorescein label or a tretramethyl rhodamine label. Most preferably, at least two different labels are used to label the different primers which are used in the multiplex amplification reaction.

The at least one DNA sample to be analyzed using the method of this invention is preferably isolated from human tissue, preferably tissue selected from the group consisting of blood, semen, vaginal cells, hair, saliva, urine, bone, buccal samples, amniotic fluid containing placental cells or fetal cells, and mixtures of any of the tissues listed above.

In an alternative embodiment, the invention is a kit for simultaneously analyzing STR sequences in at least three loci, the kit comprising a container which has oligonucleotide primer pairs for co-amplifying a set of at least three short tandem repeat loci, wherein the set of loci are selected from the sets of loci consisting of:

D3S1539, D19S253, D13S317;
D10S1239, D9S930, D20S481;
D10S1239, D4S2368, D20S481;
D10S1239, D9S930, D4S2368;
D16S539, D7S820, D13S317;
D10S1239, D9S930, D13S317;
D3S1539, D7S820, D13S317, D5S818;

D17S1298, D7S820, D13S317, D5S818;
D20S481, D7S820, D13S317, D5S818;
D9S930, D7S820, D13S317, D5S818;
D10S1239, D7S820, D13S317, D5S818;
D14S118, D7S820, D13S317, D5S818;
D14S562, D7S820, D13S317, D5S818;
D14S548, D7S820, D13S317, D5S818;
D16S490, D7S820, D13S317, D5S818;
D17S1299, D7S820, D13S317, D5S818;
D16S539, D7S820, D13S317, D5S818;
D22S683, D7S820, D13S317, D5S818;
D16S753, D7S820, D13S317, D5S818;
D3S1539, D19S253, D13S317, D20S481;
D3S1539, D19S253, D4S2368, D20S481;
D10S1239, D9S930, D4S2368, D20S481;
D16S539, D7S820, D13S317, HUMvWFA31;
D16S539, D7S820, D13S317, D5S818, HUMCSF1PO, HUMTPOX;
D16S539, D7S820, D13S317, D5S818, HUMF13A01, HUMFESFPS;
D16S539, D7S820, D13S317, D5S818, HUMCSF1PO, HUMTPOX, HUMTH01;
D16S539, D7S820, D13S317, D5S818, HUMF13A01, HUMFESFPS, HUMBFXIII;
D16S539, D7S820, D13S317, D5S818, HUMCSF1PO, HUMTPOX, HUMTH01, HUMvWFA31; and
D16S539, D7S820, D13S317, D5S818, HUMF13A01, HUMFESFPS, HUMBFXIII, HUMLIPOL.

At least one of the primers in each primer pair included in the kit preferably has a sequence selected from one of the groups of sequences listed under the description of the method of this invention, above.

In yet a third embodiment, the invention is primer sequences and primer pairs for amplifying specific STR loci of human DNA. Use of the primers and primer pairs of this invention for multiplex analysis of human DNA is demonstrated herein below. The primers of this invention are suitable for use in the method of this invention, wherein they can be used in either labeled or unlabeled form depending, as noted above, upon how the amplified alleles are to be determined in the evaluating step of the method.

The present invention, in all its various embodiments described briefly above, provides a high throughput method and materials for the detection and analysis of polymorphic genetic markers using specific combinations of loci and specified conditions. By selection of the appropriate detection technique for the evaluation step, the materials and method of this invention can be used in laboratories which have only a power supply and a standard apparatus for polyacrylamide gel electrophoresis or those which have the latest in equipment for fluorescent gel scanning, e.g., FluorImager™ 575 (Molecular Dynamics, Sunnyvale, Calif.) or the Hitachi FMBIO™ (San Bruno, Calif.) fluorescent scanners or the ABI 373 and ABI Prism™ 377 DNA Sequencers (Applied Biosystems Division, Perkin Elmer, Foster City, Calif.). Thus, the method of the present invention is adaptable for a variety of uses and laboratories.

The approach as specified in the present invention produces a savings in time, labor and materials in the analysis of loci contained within the multiplexes. The method of the present invention allows three or more, even as many as eight or more, loci to be amplified together in one tube using a single amplification reaction, instead of amplifying each locus independently in separate tubes.

The present invention has specific use in the field of forensic analysis, paternity determination, monitoring of bone marrow transplantation, linkage mapping, and detection of genetic diseases and cancers. By allowing three or more loci to be amplified and analyzed simultaneously, the materials and methods of the present invention significantly increase the certainty with which one can match DNA isolated from the blood or other tissues of two different individuals. The need to distinguish accurately between small amounts of tissue of different individuals is particularly acute in forensics applications, where many convictions (and acquittals) turn on DNA typing analysis, including the analysis of STR loci.

Scientists, particularly forensic scientists, have long appreciated the need to analyze multiple polymorphic loci of DNA in order to ensure that a match between two samples of tissue is statistically significant. (Presley, L. A. et al. (1993) "The implementation of the polymerase chain reaction (PCR) HLA DQ alpha typing by the FBI laboratory," in "The Third International Symposium on Human Identification 1992," pp. 245–269; Bever, R. A., et al. (1992) "Characterization of five VNTR loci by Hae III RFLP analysis: application to paternity testing," in "The Second International Symposium on Human Identification 1991," pp. 103–128.) However, until this invention, there were few ways one could simultaneously analyze three or more STR loci in a single reaction. To realize the importance of such multiplexing capabilities, it helps to understand some of the mathematics behind DNA typing analysis.

For purposes of illustration, suppose every STR locus has a genotype (i.e., pattern of two alleles) frequency of one in ten. In other words, suppose that the chance of two randomly selected individuals have a matching type for a single STR is 1/10. However, if two different STR loci are analyzed, the chance of a random match with both systems becomes 1/100. If three STR loci are analyzed, the chances of a random match with each of the three systems become 1/1,000 and so on. Consequently, it is easy to see how increasing the number of STR loci analyzed to any number of loci over three significantly reduces the likelihood of random matches within the general population, thereby increasing the chance one can accurately identify (or eliminate) a suspect in a crime by comparing his type with crime scene evidence. Similar reasoning can be used to conclude that the method of this invention also would increase the likelihood of accurately identifying a suspected father in a paternity case, of correctly matching bone marrow tissue, of developing significant results from linkage mapping studies, and of detecting genetic diseases and cancers.

Further objects, features, and advantages of the invention will be apparent from the following detailed description of the invention and the illustrative drawings.

DETAILED DESCRIPTION OF THE INVENTION

A. Definitions

Figure 1:
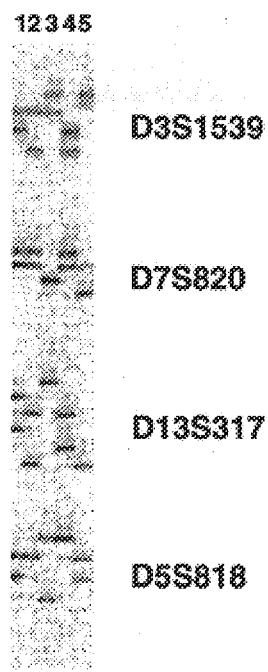
FIG. 1 is a laser-printed image showing the fluorescent detection of the products of simultaneous amplification of the loci D3S1539, D7S820, D13S317, and D5S818 as detected with a FluorImager™ fluorescent scanner (Molecular Dynamics, Sunnyvale, Calif.) in Example 1.

The following definitions are intended to assist in providing a clear and consistent understanding of the scope and detail of the terms:

Allelic ladder: a standard size marker consisting of amplified alleles from the locus.

Allele: a genetic variation associated with a segment of DNA, i.e., one of two or more alternate forms of a DNA sequence occupying the same locus.

Biochemical nomenclature: standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP).

DNA polymorphism: the condition in which two or more different nucleotide sequences in a DNA sequence coexist in the same interbreeding population.

Locus (or genetic locus): a specific position on a chromosome. Alleles of a locus are located at identical sites on homologous chromosomes.

Locus-specific primer: a primer that specifically hybridizes with a portion of the stated locus or its complementary strand, at least for one allele of the locus, and does not hybridize efficiently with other DNA sequences under the conditions used in the amplification method.

Polymerase chain reaction (PCR): a technique in which cycles of denaturation, annealing with primer, and extension with DNA polymerase are used to amplify the number of copies of a target DNA sequence by approximately $10^6$ times or more. The polymerase chain reaction process for amplifying nucleic acid is covered by U. S. Pat. Nos. 4,683,195 and 4,683,202, which are incorporated herein by reference for a description of the process.

Polymorphic short tandem repeat loci: STR loci in which the number of repetitive sequence elements (and net length of sequence) in a particular region of genomic DNA varies from allele to allele, and from individual to individual.

Polymorphism information content (PIC): a measure of the amount of polymorphism present at a locus (Botstein et al., 1980). PIC values range from 0 to 1.0, with higher values indicating greater degrees of polymorphism. This measure generally displays smaller values than the other commonly used measure, i.e., heterozygosity. For markers that are highly informative (heterozygosities exceeding about 70%), the difference between heterozygosity and PIC is slight.

Primary reaction: initial reaction using the purified human genomic DNA as template for the PCR.

Primers: two single-stranded oligonucleotides or DNA fragments which hybridize with opposing strands of a locus such that the 3' termini of the primers are in closest proximity.

Primer pair: two primers including, primer 1 that hybridizes to a single strand at one end of the DNA sequence to be amplified and primer 2 that hybridizes with the other end on the complementary strand of the DNA sequence to be amplified.

Primer site: the area of the target DNA to which a primer hybridizes.

Secondary reaction: reamplification with the same or different primer pair using a dilution of the primary reaction as template for the PCR.

Short tandem repeat loci (STR loci): regions of the human genome which contain short, repetitive sequence elements of 3 to 7 base pairs in length.

B. Selection of Multiplex Reaction Components

The method of the present invention contemplates selecting an appropriate set of loci, primers, and amplification protocols to generate amplified alleles from multiple co-amplified loci which either do not overlap in size or which are labeled in some way to make the amplified alleles which do overlap in size distinguishable from one another. In addition, this method contemplates the selection of short tandem repeat loci which are compatible for use with a single amplification protocol. The specific combinations of loci described herein are unique in this application. Combinations of loci may be rejected for either of the above two reasons, or because, in combination, one or more of the loci do not produce adequate product yield, or fragments which do not represent authentic alleles are produced in this reaction.

Successful combinations in addition to those disclosed herein can be generated by trial and error of locus combinations, by selection of primer pair sequences, and by adjustment of primer concentrations to identify an equilibrium in which all included loci may be amplified. Once the method and materials of this invention are disclosed, various methods of selecting loci, primer pairs, and amplification techniques for use in the method and kit of this invention are likely to be suggested to one skilled in the art. All such methods are intended to be within the scope of the appended claims.

Of particular importance in the practice of the method of this invention is the size range of amplified alleles produced from the individual loci which are amplified together in the multiplex amplification reaction step. For ease of analysis with current technologies, systems which can be detected by amplification of fragments smaller than 500 bases are most preferable. The most preferable combinations of loci, primers, and amplification techniques are described in the Summary of the Invention section, above.

Inappropriate selection of primers can produce several undesirable effects such as lack of amplification, amplification at multiple sites, primer dimer formation, undesirable interaction of primer sequences from different loci, production of alleles from one locus which overlap with alleles from another, or the need for amplification conditions or protocols for the different loci which are incompatible in a multiplex. Synthesis of the primers used in the present method can be conducted using any standard procedure for oligonucleotide synthesis known to those skilled in the art.

C. Use of Multiplexes of Three Loci to Develop Multiplexes Using More than Three Loci Any one of a number of different techniques can be used to select the set of STR loci to be analyzed using a method of the present invention. One preferred technique for developing useful sets of loci for use in this method of analysis is described below. Once a multiplex containing three loci is developed, it may be used as a core to create multiplexes containing more than three loci. New combinations are created including the first three loci. For example, the core multiplex containing loci D7S820, D13S317, and D5S818 was used to generate derivative multiplexes of D16S539, D7S820, D13S317, and D5S818; HUMCSF1PO, HUMTPOX, D16S539, D7S820, D13S317, and D5S818; HUMCSF1PO, HUMTPOX, HUMTH01, D16S539, D7S820, D13S317, and D5S818; and HUMCSF1PO, HUMTPOX, HUMTH01, HUMvWFA31, D16S539, D7S820, D13S317, and D5S818.

It is contemplated that core sets of loci can be used to generate other appropriate derivative sets of STR loci for multiplex analysis using the method of this invention. Regardless of what method is used to select the loci analyzed using the method of the present invention, all the loci selected for multiplex analysis should share the following characteristics: (1) they should produce minimal slippage (e.g., from misreading the repeat sequence during an amplification step), (2) few if any artifacts due to the addition or deletion of a base to the amplified alleles during the multiplex amplification step, (3) few if any artifacts due to premature termination of amplification reactions by a polymerase, and (4) no "trailing" bands of smaller molecular weight from consecutive single base deletions below a given authentic amplified allele. See, e.g., Schumm et al., "Development of Nonisotopic Multiplex Amplification Sets for Analysis of Polymorphic STR Loci," *Fourth International Symposium on Human Identification* 1993, pp. 177–187 (pub. by Promega Corp., 1993).

D. Preparation of DNA Samples

Samples of human genomic DNA can be prepared for use in the method of this invention using any method of DNA preparation which is compatible with the amplification of a single locus. Many such methods are suitable for use in preparing genomic DNA samples for use in the method of this invention, including, but not limited to, the methods of DNA sample preparation described by Patel, P. I., et al. (1984) "Organization of the HPRT gene and related sequences in the human genome," *Somat Cell Mol Genet* 10: 483–493, and Gill, P., et al. (1985) "Forensic application of DNA 'fingerprints'," *Nature* 318: 577–579.

DNA concentrations can be measured prior to use in the method of the present invention, using any standard method of DNA detection. However, the DNA concentration is preferably measured fluorometrically using a measurement technique such as that described by Brunk C. F., et al. 4 (1979) "Assay for nanogram quantities of DNA in cellular homogenates," *Anal Biochem* 92: 497–500. The DNA concentration is more preferably measured by comparison of the amount of hybridization of DNA standards with a human-specific probe such as that described by Waye et al. (1979) Waye, J. S., et al. (1991) "Sensitive and specific quantification of human genomic deoxyribonucleic acid (DNA) in forensic science specimens: casework examples," *J. Forensic Sci.,* 36:1198–1203. Use of too much template DNA in the amplification reactions can produce artifacts which appear as extra bands which do not represent true alleles.

E. Amplification of DNA

Once a sample of human genomic DNA is isolated, and its concentration determined as described above, the targeted loci can be co-amplified in the multiplex amplification step of the present method. Any one of a number of different amplification methods can be used to amplify the loci, including, but not limited to, polymerase chain reaction (PCR) (Saiki, R. K., et al. (1985) "Enzymatic amplification of beta-globin genomic sequences and restriction site analysis for diagnosis of sickle cell anemia," *Science* 230: 1350–1354), transcription based amplification (Kwoh, D. Y., and Kwoh, T. J. (1990) "Target amplification systems in nucleic acid-based diagnostic approaches," *American Biotechnology Laboratory, October,* 1990) and strand displacement amplification (SDA) (Walker, G. T., et al. (1992) "Isothermal in vitro amplification of DNA by a restriction enzyme-DNA Polymerase system," *Proc. Natl. Acad. Sci., U.S.A.* 89: 392–396). Preferably, the DNA sample is subjected to PCR amplification using primer pairs and thermocycling conditions specific to each locus in the set. Reference is made to the Sequence Listing at the end of this specification for details of the primer sequences used in the Examples below, some of which sequences are alternative embodiments of this invention.

Details of the most preferred amplification protocol for each of the most preferred combinations of loci for use in the method of this invention are given in the examples below. Reference is also made to the examples for additional details of the specific procedure relating to each multiplex. The sequences of the locus-specific primers used in the examples include a number of nucleotides which, under the conditions used in the hybridization, are sufficient to hybridize with an allele of the locus to be amplified and to be essentially free from amplification of alleles of other loci. Reference is made to U.S. Pat. No. 5,192,659 to Simons, the teaching of which is incorporated herein by reference for a more detailed description of locus-specific primers.

F. Separation and Detection of DNA Fragments

Once a set of amplified alleles is produced from the multiplex amplification step of the present method, the amplified alleles are evaluated. The evaluation step of this method can be accomplished by any one of a number of different means, the most preferred of which are described below.

Electrophoresis is preferably used to separate the products of the multiplex amplification reaction, more preferably denaturing polyacrylamide gel electrophoresis (see, e.g., Sambrook, J. et al. (1989) *In Molecular Cloning-A Laboratory Manual,* 2nd edition, Cold Spring Harbor Laboratory Press, pp. 13.45–13.57). The most preferred gel preparation and electrophoresis procedures and conditions for use in the evaluating step of the method of this invention are described in Example 1. Separation of DNA fragments in a denaturing polyacrylamide gel occurs based on fragment size.

Once the amplified alleles are separated in a polyacrylamide gel, the alleles and any other DNA in the gel (e.g., DNA markers or an allelic ladder) can then be visualized and analyzed. Visualization of the DNA in the gel can be accomplished using any one of a number of prior art techniques, including silver staining or reporters such as radioisotopes, fluorescers, chemiluminescers and enzymes in combination with detectable substrates. Silver staining is a preferred method of visualizing the alleles in the gel (see, e.g., Bassam, B. J., et al. (1991) "Fast and sensitive silver staining of DNA in polyacrylamide gels," *Anal. Biochem.* 196: 80–83). A more preferred method is the use of radioactively-labeled (see, e.g., Hammond et al., (1994)) or fluorescently-labeled (see, e.g., Schumm et al., (1994)) primers for each locus in the multiplexing reaction followed by detection of the labeled products using an autoradiogram or fluorometric detector, respectively. All three references, cited above, which describe prior art methods of visualizing alleles, are incorporated by reference herein.

The alleles present in the DNA sample are preferably determined by comparison to a size standard such as a DNA marker or a locus-specific allelic ladder to determine the alleles present at each locus within the sample. The most preferred size marker for evaluation of a multiplex amplification containing two or more polymorphic STR loci consists of a combination of allelic ladders for each of the loci being evaluated. See, e.g., description of allelic ladders and method of ladder construction in Schumm et al., supra, at p. 178.

The preferred size marker for evaluation of a multiplex amplification containing two or more polymorphic STR loci which are generated using fluorescently-labeled primers for each locus consists of a combination of fluorescently-labeled allelic ladders for the loci being evaluated. Id.

Following the construction of allelic ladders for individual loci, they may be mixed and loaded for gel electrophoresis at the same time as the loading of amplified samples occurs. Each allelic ladder co-migrates with alleles in the sample from the corresponding locus.

A permanent record of the data can be generated using Automatic Processor Compatible (APC) film (STR systems manual #TMD004, available from Promega Corporation, Madison, Wis.) or with use of a fluorescent detection instrument (STR systems manual #TMD006, also available from Promega Corporation, Madison, Wis.).

G. Preferred Detection Technique: Fluorescent Detection

In one of the most preferred embodiments of the method of this invention, fluorescent detection is used to evaluate the amplified alleles in the mixture produced by the multiplex amplification reaction. Below is a brief summary of how that method of detection preferably is practiced.

With the advent of automated fluorescent imaging, faster detection and analysis of multiplex amplification products can be achieved. For fluorescent analyses, one fluoresceinated primer can be included in the amplification of each locus. Descriptions of the use of two preferred species of fluorescent labeled primers, fluorescein-labeled (FL-) and tetramethyl rhodamine-labeled (TMR-) primers are included in the examples, below. Separation of the amplified fragments produced using such labeled primers is achieved in precisely the same manner as with the silver stain detection method. The resulting gel can be analyzed using a FluorImager™ analyzer (commercially available from Molecular Dynamics, Sunnyvale, Calif.) or FMBIO™ (commercially available from Hitachi Corporation, San Bruno, Calif.), which scans the gel and digitizes the data in a very short time, e.g., three to twenty minutes.

In summary, the method of this invention is most preferably practiced using fluorescent detection at the evaluating step. In this preferred method of detection, one of each pair of primers used in the multiplex amplification reaction has a fluorescent label attached thereto, and as a result, the amplified alleles produced from the amplification reaction are fluorescently labeled. In this most preferred embodiment of the invention, the amplified alleles are subsequently separated on a polyacrylamide gel and the separated alleles visualized and analyzed using a fluorescent image analyzer.

Fluorescent detection is preferred over radioactive methods of labeling and detection, because it does not require the use of radioactive materials, and all the regulatory and safety problems which accompany the use of such materials.

Fluorescent detection is also preferred over other non-radioactive methods of detection, such as silver staining, because fluorescent methods of detection generally reveal fewer gel artifacts than staining. The smaller number of gel artifacts are probably due, to a large extent, to the fact that only amplified fragments of DNA with labels attached are detected in fluorescent detection, while every amplified fragment of DNA produced from the multiplex amplification reaction is stained and detected using the silver staining method of detection. Polyacrylamide gels stained with silver stain also have a considerably higher general background due to nonspecific binding of silver stain to the gel itself, reducing the sensitivity with which individual bands of DNA can be detected within the gel. Silver staining and fluorescent methods of detection are compared in two sets of examples, hereinbelow.

H. Kit

The present invention is also directed to kits that utilize the process described above. A basic kit comprises a container having one or more locus-specific primers for each locus. Instructions for use optionally may be included.

Other optional kit components may include an allelic ladder directed to each of the specified loci, a sufficient quantity of enzyme for amplification, amplification buffer to facilitate the amplification, loading solution for preparation of the amplified material for gel electrophoresis, human genomic DNA as a template control, a size marker to insure that materials migrate as anticipated in the gel, and a protocol and manual to educate the user and to limit error in use. The amounts of the various reagents in the kits also can be varied depending upon a number of factors, such as the optimum sensitivity of the process. It is within the scope of this invention to provide test kits for use in manual applications or test kits for use with automated detectors or analyzers.

EXAMPLES

The following examples are presented to illustrate the advantages of the present invention and to assist one of ordinary skill in making and using the same. The examples are not intended in any way to otherwise limit the scope of the disclosure or protection granted by the patent.

Genomic DNA isolation and quantitation were performed essentially as described by Puers, C., et al. (1993) "Identification of repeat sequence heterogeneity at the polymorphic short tandem repeat locus HUMTH01 [AATG]$_n$ and reassignment of alleles in population analysis by using a locus-specific allelic ladder," *Am. J. Hum. Genet.* 53: 953–958. These methods are generally known to those skilled in the art and are preferred, but not required, for application of the invention.

Amplification products were separated by electrophoresis through a 0.4 mm thick 4% denaturing polyacrylamide gel (19:1 ratio of acrylamide to bis-acrylamide) which contained 7M urea (Sambrook et al., (1989)), and which was chemically cross-linked to a glass plate (Kobayashi, Y. (1988) "A method to cast thin sequencing gels," *BRL Focus* 10: 73–74) in cases involving silver stain analysis. No such cross-linking was employed in cases involving fluorescent analysis. DNA samples were mixed with 2.5 μl of a loading solution (10 MM NaOH, 95% formamide, 0.05% bromophenol blue, 0.05% xylene cyanol), denatured at 95° C. for 2 min., and chilled on ice prior to loading.

Once separated by polyacrylamide gel electrophoresis, the amplified reaction products and DNA size marker controls were detected using silver staining, fluorescent detection, radioactive detection, or a combination of the above detection methods. In some Examples, the reaction products and size markers in the gel were detected by silver staining using a standard method of staining and detection described in the prior art. (See, e.g., Bassam et al., (1991).) Permanent images of the stained gels were obtained by exposure to Automatic Processor Compatible Film (APC Film, Promega Corporation, Cat. No. DQ4411). In other Examples, detection was performed by fluorescent scanning, using a method described in the prior art (Schumm et al., (1994)).

Each example below is an example of the use of the method of this invention, and in some cases, an example of the use of one or more of the primers of this invention to determine simultaneously the alleles present in at least three short tandem repeat loci from one or more DNA samples. Tables 1 and 2 summarize which set of loci was co-amplified in the multiplex amplification reaction described in each Example below. The two tables also indicate which primer pair was used to amplify each such locus in each such multiplex reaction. Table 1 lists all the Examples where fluorescent scanning was used to detect the amplified alleles from the multiplex reactions described therein, while Table 2 lists the Examples where silver staining was used to detect the amplified alleles.

One primer of each primer pair listed on Table 1 was fluorescently labeled prior to being used in the multiplex amplification reaction. In some cases, a different label was used to label primers to different loci, such that the alleles produced using the different primers could be distinguished from one another when scanned by the fluorescent scanner used in the Examples below. Two different fluorescent labels were used in the Examples below, described as "FL" to indicate fluorescein-labeled and "TMR" to indicate tetramethyl rhodamine-labeled in Table 1, below. Table 1 also indicates which primer of each pair of primers used in the multiplex amplification reaction was so labeled in each example (e.g., "FL-2" means the primer with SEQ ID NO:2 was labeled at its 5' end with fluorescein prior to being used in the multiplex amplification reaction).

The same FL and TMR abbreviations are used in the Examples below. However, there the label abbreviation is placed immediately before the SEQ ID NO of the labeled primer used in the amplification reaction described therein (e.g., "FL-SEQ ID NO:2" instead of "FL-2").

In four pairs of Examples below (Examples 2 and 3, 4 and 5, 7 and 8, and 19 and 23), the same set of loci were analyzed using the same set of primers and the same fluorescent labels covalently attached to one of each pair of primers for each STR locus analyzed. However, a different set of primers was labeled in each of the Examples. These pairs of Examples are included herein to demonstrate that the same low background and identical allelic determination results can be obtained from the same set of primers using fluorescent labeling as a method of detection, no matter which of the primers of a primer pair is labeled prior to being used in a multiplex amplification reaction of the method of this invention.

TABLE 1

| Example | Loci Amplified | Primer Pair: SEQ ID NO:'s | Fluorescent Label(s) Used |
|---|---|---|---|
| 1 | D7S820 | 1, 2 | FL-2 |
|   | D13S317 | 3, 4 | FL-4 |
|   | D5S818 | 5, 6 | FL-6 |
|   | D3S1539 | 7, 8 | FL-8 |
| 2 | D7S820 | 1, 2 | FL-2 |
|   | D13S317 | 3, 4 | FL-4 |
|   | D5S818 | 5, 6 | FL-6 |
|   | D17S1298 | 9, 10 | FL-10 |
| 3 | D7S820 | 1, 2 | FL-2 |
|   | D13S317 | 3, 4 | FL-4 |
|   | D5S818 | 5, 6 | FL-6 |
|   | D17S1298 | 9, 10 | FL-9 |
| 4 | D7S820 | 1, 2 | FL-2 |
|   | D13S317 | 3, 4 | FL-4 |
|   | D5S818 | 5, 6 | FL-6 |
|   | D20S481 | 11, 12 | FL-12 |
| 5 | D7S820 | 1, 2 | FL-2 |
|   | D13S317 | 3, 4 | FL-4 |
|   | D5S818 | 5, 6 | FL-6 |
|   | D20S481 | 11, 12 | FL-11 |
| 6 | D7S820 | 1, 2 | FL-2 |
|   | D13S317 | 3, 4 | FL-4 |
|   | D5S818 | 5, 6 | FL-6 |
|   | D9S930 | 13, 14 | FL-14 |
| 7 | D7S820 | 1, 2 | FL-2 |
|   | D13S317 | 3, 4 | FL-4 |
|   | D5S818 | 5, 6 | FL-6 |
|   | D10S1239 | 15, 16 | FL-16 |
| 8 | D7S820 | 1, 2 | FL-2 |
|   | D13S317 | 3, 4 | FL-4 |
|   | D5S818 | 5, 6 | FL-6 |
|   | D10S1239 | 15, 16 | FL-15 |
| 9 | D7S820 | 1, 2 | FL-2 |
|   | D13S317 | 3, 4 | FL-4 |
|   | D5S818 | 5, 6 | FL-6 |
|   | D14S118 | 17, 18 | FL-18 |
| 10 | D7S820 | 1, 2 | FL-2 |
|   | D13S317 | 3, 4 | FL-4 |
|   | D5S818 | 5, 6 | FL-6 |
|   | D14S562 | 19, 20 | FL-19 |
| 11 | D7S820 | 1, 2 | FL-2 |
|   | D13S317 | 3, 4 | FL-4 |
|   | D5S818 | 5, 6 | FL-6 |
|   | D14S548 | 21, 22 | FL-22 |
| 12 | D7S820 | 1, 2 | FL-2 |
|   | D13S317 | 3, 4 | FL-4 |
|   | D5S818 | 5, 6 | FL-6 |
|   | D16S490 | 23, 24 | FL-23 |
| 13 | D7S820 | 1, 2 | FL-2 |
|   | D13S317 | 3, 4 | FL-4 |
|   | D5S818 | 5, 6 | FL-6 |
|   | D16S753 | 25, 26 | FL-26 |
| 14 | D7S820 | 1, 2 | FL-2 |
|   | D13S317 | 3, 4 | FL-4 |
|   | D5S818 | 5, 6 | FL-6 |
|   | D17S1299 | 27, 28 | FL-28 |
| 15 | D7S820 | 1, 2 | FL-2 |
|   | D13S317 | 3, 4 | FL-4 |
|   | D5S818 | 5, 6 | FL-6 |
|   | D16S539 | 29, 30 | FL-30 |
| 16 | D7S820 | 1, 2 | FL-2 |
|   | D13S317 | 3, 4 | FL-4 |
|   | D5S818 | 5, 6 | FL-6 |
|   | D22S683 | 31, 32 | FL-32 |
| 17 | D7S820 | 1, 2 | FL-2 |
|   | D13S317 | 3, 4 | FL-4 |
|   | D5S818 | 5, 6 | FL-6 |
|   | D16S539 | 29, 30 | FL-30 |
|   | HUMCSF1PO | 33, 34 | TMR-33 |
|   | HUMTPOX | 35, 36 | TMR-36 |
| 18 | D7S820 | 1, 2 | FL-2 |
|   | D13S317 | 3, 4 | FL-4 |
|   | D5S818 | 5, 6 | FL-6 |
|   | D16S539 | 29, 30 | FL-30 |
|   | HUMCSF1PO | 33, 34 | TMR-33 |
|   | HUMTPOX | 35, 36 | TMR-36 |
|   | HUMTH01 | 37, 38 | TMR-38 |

TABLE 1-continued

| Example | Loci Amplified | Primer Pair: SEQ ID NO:'s | Fluorescent Label(s) Used |
|---|---|---|---|
| 19 | D7S820 | 1, 2 | FL-2 |
| | D13S317 | 3, 4 | FL-4 |
| | D5S818 | 5, 6 | FL-6 |
| | D16S539 | 29, 30 | FL-30 |
| | HUMCSF1PO | 33, 34 | TMR-33 |
| | HUMTPOX | 35, 36 | TMR-36 |
| | HUMTH01 | 37, 38 | TMR-38 |
| | HUMvWFA31 | 39, 40 | TMR-40 |
| 20 | D7S820 | 1, 2 | FL-2 |
| | D13S317 | 3, 4 | FL-4 |
| | D5S818 | 5, 6 | FL-6 |
| | D16S539 | 29, 30 | FL-30 |
| | HUMF13A01 | 41, 42 | TMR-41 |
| | HUMFESFPS | 43, 44 | TMR-43 |
| 21 | D7S820 | 1, 2 | FL-2 |
| | D13S317 | 3, 4 | FL-4 |
| | D5S818 | 5, 6 | FL-6 |
| | D16S539 | 29, 30 | FL-30 |
| | HUMF13A01 | 41, 42 | TMR-41 |
| | HUMFESFPS | 43, 44 | TMR-43 |
| | HUMBFXIII | 45, 46 | TMR-45 |
| 22 | D7S820 | 1, 2 | FL-2 |
| | D13S317 | 3, 4 | FL-4 |
| | D5S818 | 5, 6 | FL-6 |
| | D16S539 | 29, 30 | FL-30 |
| | HUMF13A01 | 41, 42 | TMR-41 |
| | HUMFESFPS | 43, 44 | TMR-43 |
| | HUMBFXIII | 45, 46 | TMR-45 |
| | LIPOL | 47, 48 | TMR-47 |
| 23 | D7S820 | 1, 2 | TMR-2 |
| | D13S317 | 3, 4 | TMR-4 |
| | D5S818 | 5, 6 | TMR-6 |
| | D16S539 | 29, 30 | TMR-30 |
| 24 | D3S1539 | 7, 49 | FL-49 |
| | D19S253 | 50, 51 | FL-50 |
| | D13S317 | 3, 4 | FL-4 |
| | D20S481 | 52, 53 | FL-53 |
| 25 | D10S1239 | 15, 54 | FL-15 |
| | D9S930 | 55, 14 | FL-14 |
| | D4S2368 | 56, 57 | FL-57 |
| | D20S481 | 52, 53 | FL-53 |

Note that in a few cases, the same set of loci and same set of primer pairs appear in Table 1 and in Table 2. In such cases, the same set of alleles were analyzed using fluorescent detection and silver staining, respectively. Two such cases of duplicate sets are provided herein, Examples 24 and 33, and Examples 25 and 30. These examples clearly illustrate that the same results can be obtained with either method.

TABLE 2

| Example | Loci Amplified | Primer Pair: SEQ ID NO:'s |
|---|---|---|
| 26 | D16S539 | 29, 58 |
| | D7S820 | 1, 2 |
| | D13S317 | 3, 4 |
| 27 | D16S539 | 29, 30 |
| | D7S820 | 1, 2 |
| | D13S317 | 3, 4 |
| | HUMvWFA31 | 59, 60 |
| 28 | D10S1239 | 15, 54 |
| | D9S930 | 55, 61 |
| | D13S317 | 31, 4 |
| 29 | D10S1239 | 15, 54 |
| | D9S930 | 55, 61 |
| | D4S2368 | 56, 57 |
| 30 | D10S1239 | 15, 54 |
| | D9S930 | 55, 14 |
| | D4S2368 | 56, 57 |
| | D20S481 | 52, 53 |
| 31 | D3S1539 | 7, 49 |
| | D19S253 | 50, 51 |
| | D13S317 | 3, 4 |
| 32 | D3S1539 | 7, 49 |
| | D19S253 | 50, 51 |
| | D4S2368 | 56, 57 |
| | D20S481 | 52, 53 |
| 33 | D3S1539 | 7, 49 |
| | D19S253 | 50, 51 |
| | D13S317 | 3, 4 |
| | D20S481 | 52, 53 |
| 34 | D10S1239 | 15, 54 |
| | D9S930 | 55, 14 |
| | D20S481 | 52, 53 |
| 35 | D10S1239 | 15, 54 |
| | D4S2368 | 56, 57 |
| | D20S481 | 52, 53 |

Example 1

Flourescent Detection of Multiplex Amplification of Loci D3S1539, D7S820, D13S317, and D5S818

In this example, a DNA template was amplified simultaneously at the individual loci D3S1539, D7S820, and D5S818 in a single reaction vessel. The PCR amplification was performed in 25 $\mu$l of 1× STR Buffer (50 mM KCl, 10 mM Tris-HCl (pH 9.0 at 25° C.), 0.1% Triton X-100, 1.5 mM $MgCl_2$ and 200 $\mu$M each of dATP, dCTP, dGTP and dTTP) using 5 ng template, and 0.04 U Tag DNA Polymerase/$\mu$l. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.25 $\mu$M each D3S1539 primers 1 [SEQ ID NO:7] and 2 [FL-SEQ ID NO:8], 0.325 $\mu$M each D7S820 primers 1 [SEQ ID NO:1] and 2 [FL-SEQ ID NO:2], 0.219 $\mu$M each D13S317 primers 1 [SEQ ID NO:3] and 2 [FL-SEQ ID NO:4], 0.375 $\mu$M each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Reference is made to FIG. 1 which displays the amplified fragments of each locus. Lanes 1 to 5 contain DNA samples simultaneously co-amplified for the loci D3S1539, D7S820, D13S317, and D5S818.

Example 2

Fluorescent Detection of Multiplex Amplification of Loci D17S1298. D7S820. D13S317, and D5S818

In this example, a DNA template was amplified simultaneously at the individual loci D17S1298, D7S820, D13S317, and D5S818 in a single reaction vessel. The PCR amplification was performed in 25 $\mu$l of 1× STR Buffer (50 mM KCl, 10 mM Tris-HCl (pH 9.0 at 25° C.), 0.1% Triton X-100, 1.5 mM $MgCl_2$ and 200 $\mu$M each of dATP, dCTP, dGTP and dTTP) using 5 ng template, and 0.04 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.25 μM each D17S1298 primers 1 [SEQ ID NO:9] and 2 [FL-SEQ ID NO:10], 0.325 μM each D7S820 primers 1 [SEQ ID NO:1] and 2 [FL-SEQ ID NO:2], 0.219 μM each D13S317 primers 1 [SEQ ID NO:3] and 2 [FL-SEQ ID NO:4], 0.375 μM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 2:
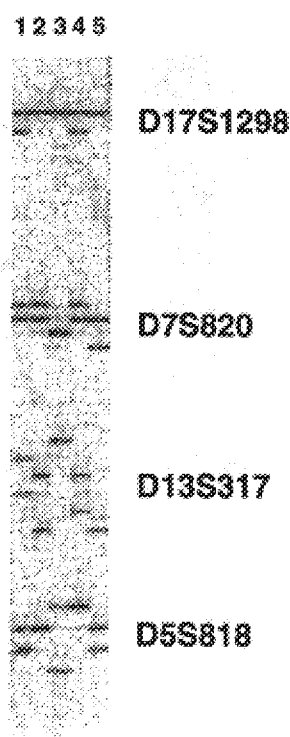
FIG. 2 is a laser-printed image showing the fluorescent detection of the products of simultaneous amplification of the loci D17S1298, D7S820, D13S317, and D5S818 as detected with a FluorImager™ fluorescent scanner (Molecular Dynamics, Sunnyvale, Calif.) in Example 2.

Reference is made to FIG. 2 which displays the amplified fragments of each locus. Lanes 1 to 5 contain DNA samples simultaneously co-amplified for the loci D17S1298, D7S820, D13S317, and D5S818.

Example 3

Fluorescent Detection of Multiplex Amplification of Loci D17S1298, D7S820, D13S317, and D5S818

The loci D17S1298, D7S820, D13S317, and D5S818 were amplified as described in Example 2 except that SEQ ID NO:9 was replaced with FL-SEQ ID NO:9 and FL-SEQ ID NO:10 was replaced with SEQ ID NO:10.

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 3:
FIG. 3 is a laser-printed image showing the fluorescent detection of the products of simultaneous amplification of the loci D17S1298, D7S820, D13S317, and D5S818 as detected with a FluorImager™ fluorescent scanner (Molecular Dynamics, Sunnyvale, Calif.) in Example 3.
Figure 3:
Figure 3:
Figure 3:
Figure 3:
Figure 3:
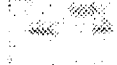
Figure 3:

Reference is made to FIG. 3 which displays the amplified fragments of each locus. Lanes 1 to 5 contain DNA samples simultaneously co-amplified for the loci D17S1298, D7S820, D13S317, and D5S818.

Example 4

Fluorescent Detection of Multiplex Amplification of Loci D20S481, D7S820, D13S317, and D5S818

In this example, a DNA template was amplified simultaneously at the individual loci D20S481, D7S820, D13S317, and D5S818 in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM $MgCl_2$ and 200 μM each of dATP, dCTP, dGTP and dTTP) using 5 ng template, and 0.04 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.25 μM each D20S481 primers 1 [SEQ ID NO:11] and 2 [FL-SEQ ID NO:12], 0.325 μM each D7S820 primers 1 [SEQ ID NO:1] and 2 [FL-SEQ ID NO:2], 0.219 μM each D13S317 primers 1 [SEQ ID NO:3] and 2 [FL-SEQ ID NO:4], 0.375 μM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 4:
FIG. 4 is a laser-printed image showing the fluorescent detection of the products of simultaneous amplification of the loci D20S481, D7S820, D13S317, and D5S818 as detected with a FluorImager™ fluorescent scanner (Molecular Dynamics, Sunnyvale, Calif.) in Example 4.
Figure 4:
Figure 4:
Figure 4:

Reference is made to FIG. 4 which displays the amplified fragments of each locus. Lanes 1 to 5 contain DNA samples simultaneously co-amplified for the loci D20S481, D7S820, D13S317, and D5S818.

Example 5

Fluorescent Detection of Multiplex Amplification of Loci D20S481, D7S820. D13S317, and D5S818

The loci D20S481, D7S820, D13S317, and D5S818 were amplified as described in Example 4 except that SEQ ID NO:11 was replaced with FL-SEQ ID NO:11 and FL-SEQ ID NO:12 was replaced with SEQ ID NO:12.

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 5:
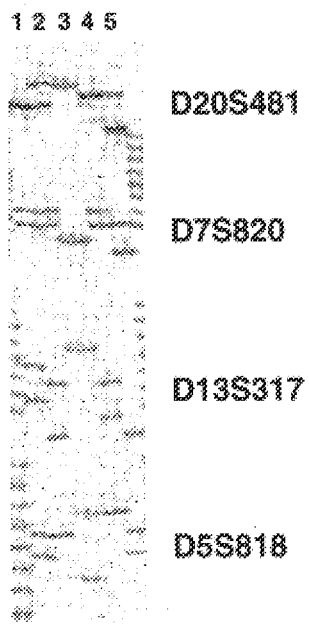
FIG. 5 is a laser-printed image showing the fluorescent detection of the products of simultaneous amplification of the loci D20S481, D7S820, D13S317, and D5S818 as detected with a FluorImager™ fluorescent scanner (Molecular Dynamics, Sunnyvale, Calif.) in Example 5.

Reference is made to FIG. 5 which displays the amplified fragments of each locus. Lanes 1 to 5 contain DNA samples simultaneously co-amplified for the loci D20S481, D7S820, D13S317, and D5S818.

Example 6

Fluorescent Detection of Multiplex Amplification of Loci D9S930. D7S820, D13S317, and D5S818

In this example, a DNA template was amplified simultaneously at the individual loci D9S930, D7S820, D13S317, and D5S818 in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM $MgCl_2$ and 200 μM each of dATP, dCTP, dGTP and dTTP) using 5 ng template, and 0.04 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.70 μM each D9S930 primers 1 [SEQ ID NO:13] and 2 [FL-SEQ ID NO:14], 0.325 μM each D7S820 primers 1 [SEQ ID NO:1] and 2 [FL-SEQ ID NO:2], 0.22 μM each D13S317 primers 1 [SEQ ID NO:3] and 2 [FL-SEQ ID NO:4], 0.375 μM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 6:
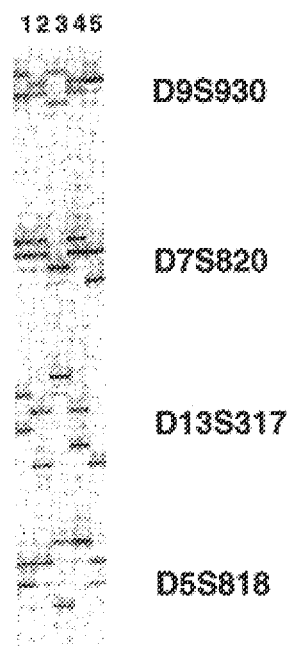
FIG. 6 is a laser-printed image showing the fluorescent detection of the products of simultaneous amplification of the loci D9S930, D7S820, D13S317, and D5S818 as detected with a FluorImager™ fluorescent scanner (Molecular Dynamics, Sunnyvale, Calif.) in Example 6.

Reference is made to FIG. 6 which displays the amplified fragments of each locus. Lanes 1 to 5 contain DNA samples simultaneously co-amplified for the loci D9S930, D7S820, D13S317, and D5S818.

Example 7

Fluorescent Detection of Multiplex Amplification of Loci D10S1239, D7S820, D13S317, and D5S818

In this example, a DNA template was amplified simultaneously at the individual loci D10S1239, D7S820, D13S317, and D5S818 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.75 µM each D10S1239 primers 1 [SEQ ID NO:15] and 2 [FL-SEQ ID NO:16], 0.325 µM each D7S820 primers 1 [SEQ ID NO:1] and 2 [FL-SEQ ID NO:2], 0.22 µM each D13S317 primers 1 [SEQ ID NO:3] and 2 [FL-SEQ ID NO:4], 0.375 µM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 7:
FIG. 7 is a laser-printed image showing the fluorescent detection of the products of simultaneous amplification of the loci D10S1239, D7S820, D13S317, and D5S818 as detected with a FluorImager™ fluorescent scanner (Molecular Dynamics, Sunnyvale, Calif.)in Example 8.

Reference is made to FIG. 7 which displays the amplified fragments of each locus. Lanes 1 to 5 contain DNA samples simultaneously co-amplified for the loci D10S1239, D7S820, D13S317, and D5S818.

Example 8

Fluorescent Detection of Multiplex Amplification of Loci D10S1239. D7S820, D13S317, and D5S818

The loci D10S1239, D7S820, D13S317, and D5S818 were amplified as described in Example 7 except that SEQ ID NO:15 was replaced with FL-SEQ ID NO:15 and FL-SEQ ID NO:16 was replaced with SEQ ID NO:16.

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 8:
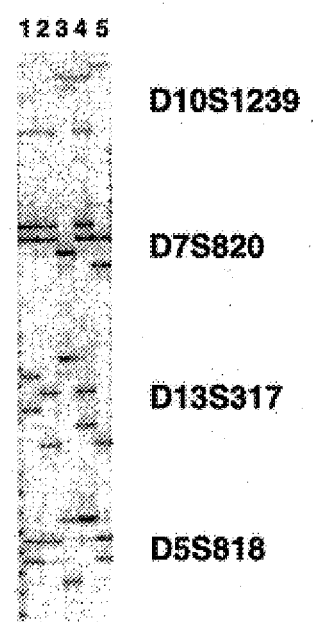
FIG. 8 is a laser-printed image showing the fluorescent detection of the products of simultaneous amplification of the loci D10S1239, D7S820, D13S317, and D5S818 as detected with a FluorImager™ fluorescent scanner (Molecular Dynamics, Sunnyvale, Calif.) in Example 8.

Reference is made to FIG. 8 which displays the amplified fragments of each locus. Lanes 1 to 5 contain DNA samples simultaneously co-amplified for the loci D10S1239, D7S820, D13S317, and D5S818.

Example 9

Fluorescent Detection of Multiplex Amplification of Loci D14S118, D7S820, D13S317, and D5S818

In this example, a DNA template was amplified simultaneously at the individual loci D14S118, D7S820, D13S317, and D5S818 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.50 µM each D14S118 primers 1 [SEQ ID NO:17] and 2 [FL-SEQ ID NO:18], 0.325 µM each D7S820 primers 1 [SEQ ID NO:1] and 2 [FL-SEQ ID NO:2], 0.22 µM each D13S317 primers 1 [SEQ ID NO:3] and 2 [FL-SEQ ID NO:4], 0.375 µM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 9:
FIG. 9 is a laser-printed image showing the fluorescent detection of the products of simultaneous amplification of the loci D14S118, D7S820, D13S317, and D5S818 as detected with a FluorImager™ fluorescent scanner (Molecular Dynamics, Sunnyvale, Calif.) in Example 9.

Reference is made to FIG. 9 which displays the amplified fragments of each locus. Lanes 1 to 5 contain DNA samples simultaneously co-amplified for the loci D14S118, D7S820, D13S317, and D5S818.

Example 10

Fluorescent Detection of Multiplex Amplification of Loci D14S562. D7S820 D13S317, and D5S818

In this example, a DNA template was amplified simultaneously at the individual loci D14S562, D7S820, D13S317, and D5S818 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.50 µM each D14S562 primers 1 [FL-SEQ ID NO:19] and 2 [SEQ ID NO:20], 0.325 µM each D7S820 primers 1 [SEQ ID NO:1] and 2 [FL-SEQ ID NO:2], 0.22 µM each D13S317 primers 1 [SEQ ID NO:3] and 2 [FL-SEQ ID NO:4], 0.375 µM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 10:
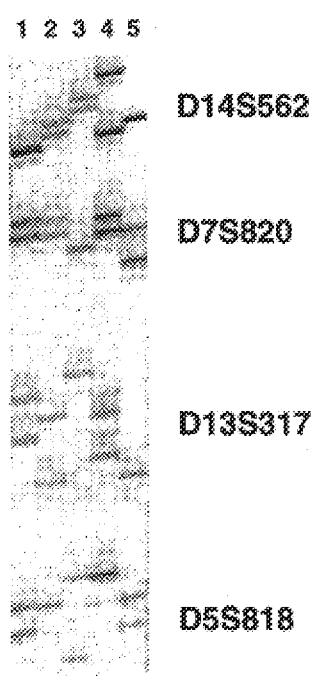
FIG. 10 is a laser-printed image showing the fluorescent detection of the products of simultaneous amplification of the loci D14S562, D7S820, D13S317, and D5S818 as detected with a FluorImager™ fluorescent scanner (Molecular Dynamics, Sunnyvale, Calif.) in Example 10.

Reference is made to FIG. 10 which displays the amplified fragments of each locus. Lanes 1 to 5 contain DNA samples simultaneously co-amplified for the loci D14S562, D7S820, D13S317, and D5S818.

Example 11

Fluorescent Detection of Multiplex Amplification of Loci D14S548, D7S820, D13S317, and D5S818

In this example, a DNA template was amplified simultaneously at the individual loci D14S548, D7S820, D13S317, and D5S818 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.50 μM each D14S548 primers 1 [SEQ ID NO:21] and 2 [FL-SEQ ID NO:22], 0.325 μM each D7S820 primers 1 [SEQ ID NO:1] and 2 [FL-SEQ ID NO:2], 0.22 μM each D13S317 primers 1 [SEQ ID NO:3] and 2 [FL-SEQ ID NO:4], 0.375 μM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 11:
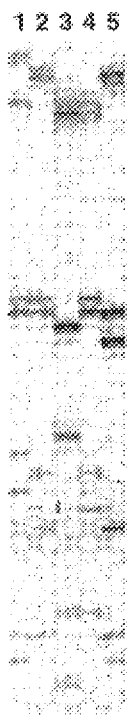
FIG. 11 is a laser-printed image showing the fluorescent detection of the products of simultaneous amplification of the loci D14S548, D7S820, D13S317, and D5S818 as detected with a FluorImager™ fluorescent scanner (Molecular Dynamics, Sunnyvale, Calif.) in Example 11.

Reference is made to FIG. 11 which displays the amplified fragments of each locus. Lanes 1 to 5 contain DNA samples simultaneously co-amplified for the loci D14S548, D7S820, D13S317, and D5S818.

Example 12

Fluorescent Detection of Multiplex Amplification of Loci D16S490, D7S820, D13S317, and D5S818

In this example, a DNA template was amplified simultaneously at the individual loci D16S490, D7S820, D13S317, and D5S818 in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM MgCl$_2$ and 200 μM each of dATP, dCTP, dGTP and dTTP) using 5 ng template, and 0.04 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.50 μM each D16S490 primers 1 [FL-SEQ ID NO:23] and 2 [SEQ ID NO:24], 0.325 μM each D7S820 primers 1 [SEQ ID NO:1] and 2 [FL-SEQ ID NO:2], 0.22 μM each D13S317 primers 1 [SEQ ID NO:3] and 2 [FL-SEQ ID NO:4], 0.375 μM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 12:
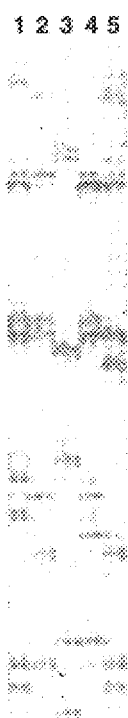
FIG. 12 is a laser-printed image showing the fluorescent detection of the products of simultaneous amplification of the loci D16S490, D7S820, D13S317, and D5S818 as detected with a FluorImager™ fluorescent scanner (Molecular Dynamics, Sunnyvale, Calif.) in Example 12.

Reference is made to FIG. 12 which displays the amplified fragments of each locus. Lanes 1 to 5 contain DNA samples simultaneously co-amplified for the loci D16S490, D7S820, D13S317, and D5S818.

Example 13

Fluorescent Detection of Multiplex Amplification of Loci D16S753, D7S820, D13S317, and D5S818

In this example, a DNA template was amplified simultaneously at the individual loci D16S753, D7S820, D13S317, and D5S818 in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM MgCl$_2$ and 200 μM each of dATP, dCTP, dGTP and dTTP) using 5 ng template, and 0.04 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.50 μM each D16S753 primers 1 [SEQ ID NO:25] and 2 [FL-SEQ ID NO:26], 0.325 μM each D7S820 primers 1 [SEQ ID NO:1] and 2 [FL-SEQ ID NO:2], 0.22 μM each D13S317 primers 1 [SEQ ID NO:3] and 2 [FL-SEQ ID NO:4], 0.375 μM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 13:
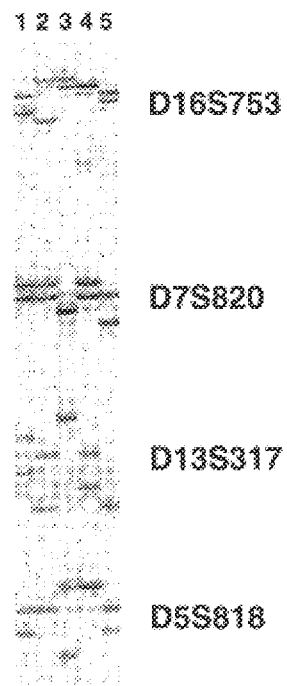
FIG. 13 is a laser-printed image showing the fluorescent detection of the products of simultaneous amplification of the loci D16S753, D7S820, D13S317, and D5S818 as detected with a FluorImager™ T fluorescent scanner (Molecular Dynamics, Sunnyvale, Calif.) in Example 13.

Reference is made to FIG. 13 which displays the amplified fragments of each locus. Lanes 1 to 5 contain DNA samples simultaneously co-amplified for the loci D16S753, D7S820, D13S317, and D5S818.

Example 14

Fluorescent Detection of Multiplex Amplification of Loci D17S1299. D7S820. D13S317, and D5S818

In this example, a DNA template was amplified simultaneously at the individual loci D17S1299, D7S820, D13S317, and D5S818 in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM MgCl$_2$ and 200 μM each of dATP, dCTP, dGTP and dTTP) using 5 ng template, and 0.04 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.50 μM each D17S1299 primers 1 [SEQ ID NO:27] and 2 [FL-SEQ ID NO:28], 0.325 μM each D7S820 primers 1 [SEQ ID NO:1] and 2 [FL-SEQ ID NO:2], 0.22 μM each D13S317 primers 1 [SEQ ID NO:3] and 2 [FL-SEQ ID NO:4], 0.375 μM each D5S818 primers 1 [SEQ ID NO:5] and 2 [FL-SEQ ID NO:6].

Amplified products were separated by denaturing polyacrylamide gel electrophoresis on a 32 cm gel for 45 min. at 40 W and products were visualized by detection of the fluorescent signals using the FluorImager™ fluorescent scanner (Molecular Dynamics, Sunnyvale, Calif.).

Figure 14:
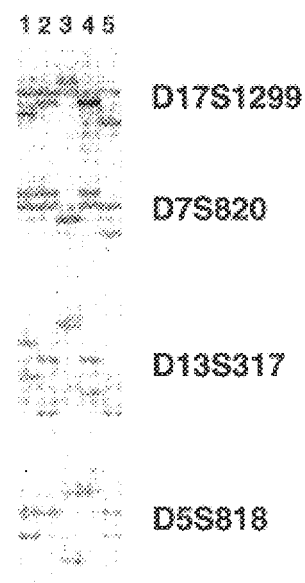
FIG. 14 is a laser-printed image showing the fluorescent detection of the products of simultaneous amplification of the loci D17S1299, D7S820, D13S317, and D5S818 as detected with a FluorImager™ fluorescent scanner (Molecular Dynamics, Sunnyvale, Calif.) in Example 14.

Reference is made to FIG. 14 which displays the amplified fragments of each locus. Lanes 1 to 5 contain DNA samples simultaneously co-amplified for the loci D17S1299, D7S820, D13S317, and D5S818.

Example 15

Fluorescent Detection of Multiplex Amplification of Loci D16S539, D7S820, D13S317, and D5S818

In this example, a DNA template was amplified simultaneously at the individual loci D16S539, D7S820, D13S317, and D5S818 in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM MgCl$_2$ and 200 μM each of dATP, dCTP, dGTP and dTTP) using 5 ng template, and 0.04 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.60 µM each D16S539 primers 1 [SEQ ID NO:29] and 2 [FL-SEQ ID NO:30], 0.325 µM each D7S820 primers 1 [SEQ ID NO:1] and 2 [FL-SEQ ID NO:2], 0.22 µM each D13S317 primers 1 [SEQ ID NO:3] and 2 [FL-SEQ ID NO:4], 0.50 µM each D5S818 primers 1 [SEQ ID NO:5] and 2 [FL-SEQ ID NO:6].

Amplified products were separated by denaturing polyacrylamide gel electrophoresis on a 32 cm gel for 50 min. at 40 W and products were visualized by detection of the fluorescent signals using the FluorImager™ fluorescent scanner (Molecular Dynamics, Sunnyvale, Calif.).

Figure 15:
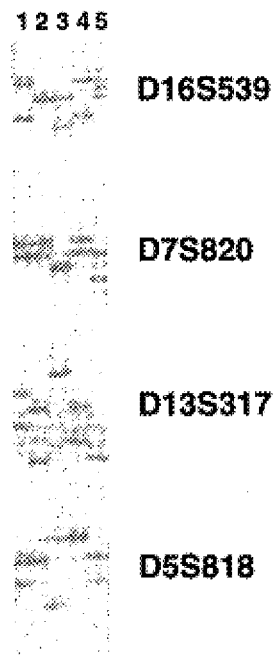
FIG. 15 is a laser-printed image showing the fluorescent detection of the products of simultaneous amplification of the loci D16S539, D7S820, D13S317, and D5S818 as detected with a FluorImager™ fluorescent scanner (Molecular Dynamics, Sunnyvale, Calif.) in Example 15.

Reference is made to FIG. 15 which displays the amplified fragments of each locus. Lanes 1 to 5 contain DNA samples simultaneously co-amplified for the loci D16S539, D7S820, D13S317, and D5S818.

Example 16

Fluorescent Detection of Multiplex Amplification of Loci D22S683, D7S820, D13S317, and D5S818

In this example, a DNA template was amplified simultaneously at the individual loci D22S683, D7S820, D13S317, and D5S818 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.50 µM each D22S683 primers 1 [SEQ ID NO:31] and 2 [FL-SEQ ID NO:32], 0.325 µM each D7S820 primers 1 [SEQ ID NO:1] and 2 [FL-SEQ ID NO:2], 0.22 µM each D13S317 primers 1 [SEQ ID NO:3] and 2 [FL-SEQ ID NO:4], 0.375 µM each D5S818 primers 1 [SEQ ID NO:5] and 2 [FL-SEQ ID NO:6].

Amplified products were separated by denaturing polyacrylamide gel electrophoresis on a 32 cm gel for 55 min. at 40 W and products were visualized by detection of the fluorescent signals using the FluorImager™ fluorescent scanner (Molecular Dynamics, Sunnyvale, Calif.).

Figure 16:
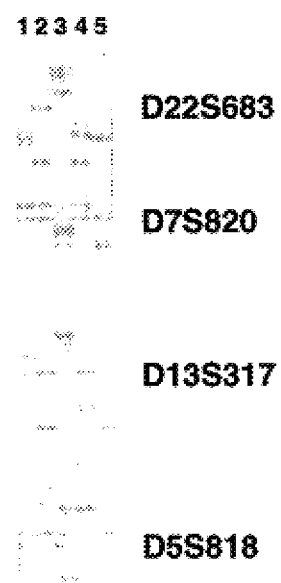
FIG. 16 is a laser-printed image showing the fluorescent detection of the products of simultaneous amplification of the loci D22S683, D7S820, D13S317, and D5S818 as detected with a FluorImager™ fluorescent scanner (Molecular Dynamics, Sunnyvale, Calif.) in Example 16.

Reference is made to FIG. 16 which displays the amplified fragments of each locus. Lanes 1 to 5 contain DNA samples simultaneously co-amplified for the loci D22S683, D7S820, D13S317, and D5S818.

Example 17

Fluorescent Detection of Multiplex Amplification of Loci D16S539, D7S820, D13S317, D5S818, HUMCSF1PO and HUMTPOX In this example, a DNA template was amplified simultaneously at the individual loci D16S539, D7S820, D13S317, D5S818, HUMCSF1PO and HUMTPOX in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 ng template, and 0.06 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Twelve amplification primers were used in combination, including 0.65 µM each D16S539 primers 1 [SEQ ID NO:29] and 2 [FL-SEQ ID NO:30], 0.325 µM each D7S820 primers 1 [SEQ ID NO:1] and 2 [FL-SEQ ID NO:2], 0.22 µM each D13S317 primers 1 [SEQ. ID NO:3] and 2 [FL-SEQ ID NO:4], 0.55 µM each D5S818 primers 1 [SEQ ID NO:5] and 2 [FL-SEQ ID NO:6], 0.40 µM each HUMCSF1PO primers 1 [TMR-SEQ ID NO:33] and 2 [SEQ ID NO:34], 0.40 µM each HUMTPOX primers 1 [SEQ ID NO:35] and 2 [TMR-SEQ ID NO:36].

Amplified products were separated by denaturing polyacrylamide gel electrophoresis on a 32 cm gel for 50 min. at 40 W and products were visualized by detection of the fluorescent signals using the FMBIOFluorImager™ (Hitachi Software Engineering, San Bruno, Calif.).

Figure 17:
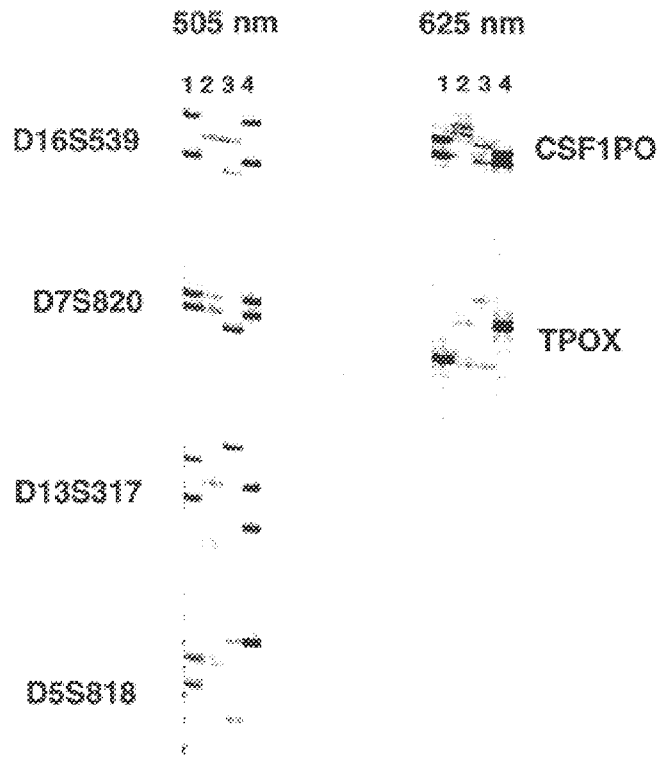
FIG. 17 is a laser-printed image showing the fluorescent detection of the products of simultaneous amplification of the loci D16S539, D7S820, D13S317, D5S818, HUMCSF1PO ("CSF1PO") and HUMTPOX ("TPOX") as detected with an FMBIO™ Fluorescent Scanner™ (Hitachi Software Engineering, San Bruno, Calif.) in Example 17.

Reference is made to FIG. 17 which displays the amplified fragments of each locus in separate 505 nm and 625 nm scans of the same gel revealing fluorescein-labeled and tetramethyl-rhodamine labeled material, respectively. Lanes 1 to 4 contain DNA samples simultaneously co-amplified for the loci D16S539, D7S820, D13S317, D5S818, HUMCSF1PO ("CSF1PO") and HUMTPOX ("TPOX").

Example 18

Fluorescent Detection of Multiplex Amplification of Loci D16S539. D7S820, D13S317, D5S818. HUMCSF1PO, HUMTPOX and HUMTH01

In this example, a DNA template was amplified simultaneously at the individual loci D16S539, D7S820, D13S317, D5S818, HUMCSF1PO, HUMTPOX and HUMTH01 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 ng template, and 0. 07 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Fourteen amplification primers were used in combination, including 0.75 µM each D16S539 primers 1 [SEQ ID NO:29] and 2 [FL-SEQ ID NO:30], 0.40 µM each D7S820 primers 1 [SEQ ID NO:1] and 2 [FL-SEQ ID NO:2], 0.30 µM each D13S317 primers 1 [SEQ ID NO:3] and 2 [FL-SEQ ID NO:4], 0.60 µM each D5S818 primers 1 [SEQ ID NO:5] and 2 [FL-SEQ ID NO:6], 0.30 µM each HUMCSF1PO primers 1 [TMR-SEQ ID NO:33] and 2 [SEQ ID NO:34], 0.40 µM each HUMTPOX primers 1 [SEQ ID NO:35] and 2 [TMR-SEQ ID NO:35], 0.40 µM each HUMTH01 primers 1 [SEQ ID NO:37] and 2 [TMR-SEQ ID NO:38].

Amplified products were separated by denaturing polyacrylamide gel electrophoresis on a 32 cm gel for 50 min. at 40 W and products were visualized by detection of the fluorescent signals using the FMBIOFluorImager™ (Hitachi Software Engineering, San Bruno, Calif.).

Figure 18:
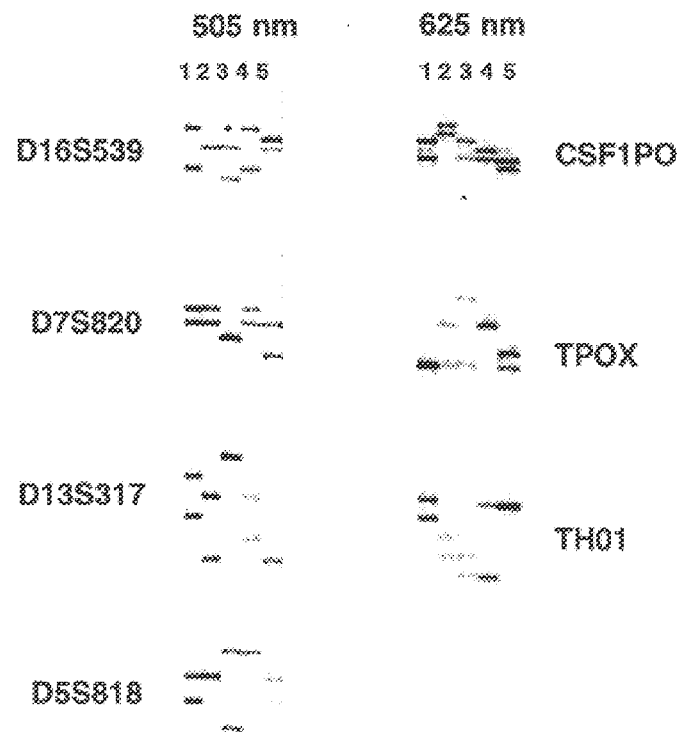
FIG. 18 is a laser-printed image showing the fluorescent detection of the products of simultaneous amplification of the loci D16S539, D7S820, D13S317, D5S818, HUMCSF1PO ("CSF1PO"), HUMTPOX ("TPOX") and HUMTH01 ("TH01") as detected with an FMBIO™ Fluorescent Scanner™ (Hitachi Software Engineering, San Bruno, Calif.) in Example 18.

Reference is made to FIG. 18 which displays the amplified fragments of each locusin separate 505 nm and 625 nm scans of the same gel revealing fluorescein-labeled and tetramethyl-rhodamine labeled material, respectively. Lanes 1 to 5 contain DNA samples simultaneously co-amplified for the loci D16S539, D7S820, D13S317, D5S818, HUMCSF1PO ("CSF1PO"), HUMTPOX ("TPOX") and HUMTH01 ("TH01").

Example 19

Fluorescent Detection of Multiplex Amplification of Loci D16S539, D7S820, D13S317, D5S818, HUMCSF1PO, HUMTPOX, HUMTH01 and HUMvWFA31

In this example, a DNA template was amplified simultaneously at the individual loci D16S539, D7S820, D13S317, D5S818, HUMCSF1PO, HUMTPOX, HUMTH01 and HUMvWFA31 in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM $MgCl_2$ and 200 μM each of dATP, dCTP, dGTP and dTTP) using 5 ng template, and 0.08 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Sixteen amplification primers were used in combination, including 0.75 μM each D16S539 primers 1 [SEQ ID NO:29] and 2 [FL-SEQ ID NO:30], 0.40 μM each D7S820 primers 1 [SEQ ID NO:1] and 2 [FL-SEQ ID NO:2], 0.30 μM each D13S317 primers 1 [SEQ ID NO:3] and 2 [FL-SEQ ID NO:4], 0.60 μM each D5S818 primers 1 [SEQ ID NO:5] and 2 [FL-SEQ ID NO:6], 0.30 μM each HUMCSF1PO primers 1 [TMR-SEQ ID NO:33] and 2 [SEQ ID NO:34], 0.40 μM each HUMTPOX primers 1 [SEQ ID NO:35] and 2 [TMR-SEQ ID NO:36], 0.40 μM each HUMTH01 primers 1 [SEQ ID NO:37] and 2 [TMR-SEQ ID NO:38], 0.40 μM each HUMvWFA31 primers 1 [SEQ ID NO:39] and 2 [TMR-SEQ ID NO:40].

Amplified products were separated by denaturing polyacrylamide gel electrophoresis on a 32 cm gel for 50 min. at 40 W and products were visualized by detection of the fluorescent signals using the FMBIOFluorImager™ (Hitachi Software Engineering, San Bruno, Calif.).

Figures 19, 20:
FIG. 19 is a laser-printed image showing the fluorescent detection of the products of simultaneous amplification of the loci D16S539, D7S820, D13S317, D5S818, HUMCSF1PO ("CSF1PO"), HUMTPOX ("TPOX"), HUMTH01 ("TH01") and HUMvWFA31 ("vWA") as detected with an FMBIO™ Fluorescent Scanner™ (Hitachi Software Engineering, San Bruno, Calif.) in Example 19.
FIG. 20 is a laser-printed image showing the fluorescent detection of the products of simultaneous amplification of the loci D16S539, D7S820, D13S317, D5S818, HUMF13A01 ("F13A01") and HUMFESFPS ("FESFPS") as detected with an FMBIO™ Fluorescent Scanner™ (Hitachi Software Engineering, San Bruno, Calif.) in Example 20.

Reference is made to FIG. 19 which displays the amplified fragments of each locus in separate 505 nm and 625 nm scans of the same gel revealing fluorescein-labeled and tetramethyl-rhodamine labeled material, respectively. Lanes 1 to 5 contain DNA samples simultaneously co-amplified for the loci D16S539, D7S820, D13S317, D5S818, HUMCSF1PO ("CSF1PO"), HUMTPOX ("TPOX"), HUMTH01 ("TH01") and HUMvWFA31 ("vWA").

Example 20

Fluorescent Detection of Multiplex Amplification of Loci D16S539, D7S820, D13S317, D5S818, HUMF13A01 and HUMFESFPS In this example, a DNA template was amplified simultaneously at the individual loci D16S539, D7S820, D13S317, D5S818, HUMF13A01 and HUMFESFPS in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM $MgCl_2$ and 200 μM each of dATP, dCTP, dGTP and dTTP) using 5 ng template, and 0.06 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Twelve amplification primers were used in combination, including 0.75 μM each D16S539 primers 1 [SEQ ID NO:29] and 2 [FL-SEQ ID NO:30], 0.40 μM each D7S820 primers 1 [SEQ ID NO:1] and 2 [FL-SEQ ID NO:2], 0.30 μM each D13S317 primers 1 [SEQ ID NO:3] and 2 [FL-SEQ ID NO:4], 0.60 μM each D5S818 primers 1 [SEQ ID NO:5] and 2 [FL-SEQ ID NO:6], 0.10 μM each HUMF13A01 primers 1 [TMR-SEQ ID NO:41] and 2 [SEQ ID NO:42], 1.0 μM each HUMFESFPS primers 1 [TMR-SEQ ID NO:43] and 2 [SEQ ID NO:44].

Amplified products were separated by denaturing polyacrylamide gel electrophoresis on a 32 cm gel for 50 min. at 40 W and products were visualized by detection of the fluorescent signals using the FMBIOFluorImager™ (Hitachi Software Engineering, San Bruno, Calif.).

Reference is made to FIG. 20 which displays the amplified fragments of each locus in separate 505 nm and 625 nm scans of the same gel revealing fluorescein-labeled and tetramethyl-rhodamine labeled material, respectively. Lanes 1 to 5 contain DNA samples simultaneously co-amplified for the loci D16S539, D7S820, D13S317, D5S818, HUMF13A10 ("F13A01") and HUMFESFPS ("FESFPS").

Example 21

Fluorescent Detection of Multiplex Amplification of Loci D16S539, D7S820, D13S317, D5S818, HUMF13A01. HUMFESFPS and HUMBFXIII In this example, a DNA template was amplified simultaneously at the individual loci D16S539, D7S820, D13S317, D5S818, HUMF13A01, HUMFESFPS and HUMBFXIII in a single reaction vessel. The PCR amplification was performed in 25 μl of 1× STR Buffer (50 mM KCl, 10 mM Tris-HCl (pH 9.0 at 25° C.), 0.1% Triton X-100, 1.5 mM $MgCl_2$ and 200 μM each of dATP, dCTP, dGTP and dTTP) using 5 ng template, and 0.07 U Taq DNA Polymerase/μl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Fourteen amplification primers were used in combination, including 0.75 μM each D16S539 primers 1 [SEQ ID NO:29] and 2 [FL-SEQ ID NO:30], 0.40 μM each D7S820 primers 1 [SEQ ID NO:1] and 2 [FL-SEQ ID NO:2], 0.30 μM each D13S317 primers 1 [SEQ ID NO:3] and 2 [FL-SEQ ID NO:4], 0.60 μM each D5S818 primers 1 [SEQ ID NO:5] and 2 [FL-SEQ ID NO:6], 0.10 μM each HUMF13A01 primers 1 [TMR-SEQ ID NO:41] and 2 [SEQ ID NO:42], 1.0 μM each HUMFESFPS primers 1 [TMR-SEQ ID NO:43] and 2 [SEQ ID NO:44], 0.50 μM each HUMBFXIII primers 1 [TMR-SEQ ID NO:45] and 2 [SEQ ID NO:46].

Amplified products were separated by denaturing polyacrylamide gel electrophoresis on a 32 cm gel for 50 min. at 40 W and products were visualized by detection of the fluorescent signals using the FNBIOFluorImager™ (Hitachi Software Engineering, San Bruno, Calif.).

Figure 21:
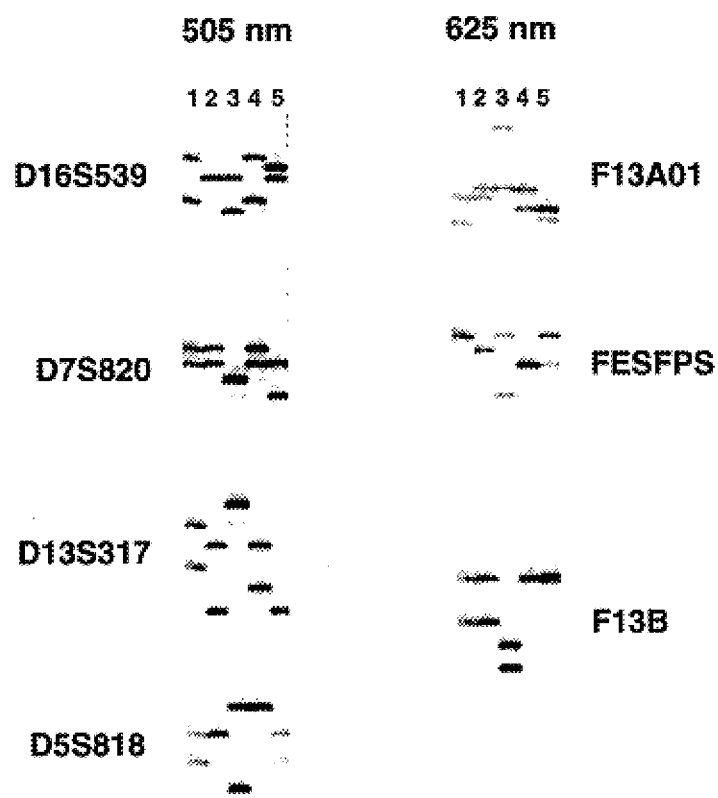
FIG. 21 is a laser-printed image showing the fluorescent detection of the products of simultaneous amplification of the loci D16S539, D7S820, D13S317, D5S818, HUMF13A01 ("F13A01"), HUMFESFPS ("FESFPS") and HUMBFXIII ("F13B") as detected with an FMBIO™ Fluorescent Scanner™ (Hitachi Software Engineering, San Bruno, Calif.) in Example 21.

Reference is made to FIG. 21 which displays the amplified fragments of each locus in separate 505 nm and 625 nm scans of the same gel revealing fluorescein-labeled and tetramethyl-rhodamine labeled material, respectively. Lanes 1 to 5 contain DNA samples simultaneously co-amplified for the loci D16S539, D7S820, D13S317, D5S818, HUMF13A01 ("F13A01"), HUMFESFPS ("FESFPS") and HUMBFXIII ("F13B").

Example 22

Fluorescent Detection of Multiplex Amplification of Loci D16S539, D7S820, D13S317, D5S818, HUMF13A10, HUMFESFPS, HUMBFXIII and HUMLIPOL In this example, a DNA template was amplified simultaneously at the individual loci D16S539, D7S820, D13S317, D5S818, HUMF13A10, HUMFESFPS, HUMBFXIII and HUMLIPOL in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 ng template, and 0.08 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Sixteen amplification primers were used in combination, including 0.75 µM each D16S539 primers 1 [SEQ ID NO:29] and 2 [FL-SEQ ID NO:30], 0.40 µM each D7S820 primers 1 [SEQ ID NO:1] and 2 [FL-SEQ ID NO:2], 0.30 µM each D13S317 primers 1 [SEQ ID NO:3] and 2 [FL-SEQ ID NO:4], 0.60 µM each D5S818 primers 1 [SEQ ID NO:5] and 2 [FL-SEQ ID NO:6], 0.10 µM each HUMF13A01 primers 1 [TMR-SEQ ID NO:41] and 2 [SEQ ID NO:42], 1.0 µM each HUMFESFPS primers 1 [TMR-SEQ ID NO:43] and 2 [SEQ ID NO:44], 0.50 µM each HUMBFXIII primers 1 [TMR-SEQ ID NO:45] and 2 [SEQ ID NO:46], 0.20 µM each HUMLIPOL primers 1 [TMR-SEQ ID NO:47] and 2 [SEQ ID NO:48].

Amplified products were separated by denaturing polyacrylamide gel electrophoresis on a 32 cm gel for 50 min. at 40 W and products were visualized by detection of the fluorescent signals using the FMBIOFluorImager™ (Hitachi Software Engineering, San Bruno, Calif.).

Figure 22:
FIG. 22 is a laser-printed image showing the fluorescent detection of the products of simultaneous amplification of the loci D16S539, D7S820, D13S317, D5S818, HUMF13A01 ("F13A01"), HUMFESFPS ("FESFPS"), HUMBFXIII ("F13B") and HUMLIPOL ("LPL") as detected with an FMBIO™ Fluorescent Scanner™ (Hitachi Software Engineering, San Bruno, Calif.) in Example 22.

Reference is made to FIG. 22 which displays the amplified fragments of each locus in separate 505 nm and 625 nm scans of the same gel revealing fluorescein-labeled and tetramethyl-rhodamine labeled material, respectively. Lanes 1 to 5 contain DNA samples simultaneously co-amplified for the loci D16S539, D7S820, D13S317, D5S818, HUMF13A01 ("HUMF13A01"), HUMFESFPS ("FESFPS"), HUMBFXIII ("F13B") and HUMLIPOL ("LPL").

Example 23

Fluorescent Detection of Multiplex Amplification of Loci D16S539. D7S820. D13S317, D5S818, HUMCSF1PO, HUMTPOX, HUMTH01 and HUMvWFA31

In this example, a DNA template was amplified simultaneously at the individual loci D16S539, D7S820, D13S317, D5S818, HUMCSF1PO, HUMTPOX, HUMTH01 and HUMvWFA31 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 ng template, and 0.08 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Sixteen amplification primers were used in combination, including 0.75 µM each D16S539 primers 1 [SEQ ID NO:29] and 2 [TMR-SEQ ID NO:30], 0.40 µM each D7S820 primers 1 [SEQ ID NO:1] and 2 [TMR-SEQ ID NO:2], 0.30 µM each D13S317 primers 1 [SEQ ID NO:3] and 2 [TMR-SEQ ID NO:4], 0.60 µM each D5S818 primers 1 [SEQ ID NO:5] and 2 [TMR-SEQ ID NO:6], 0.40 µM each HUMCSF1PO primers 1 [FL-SEQ ID NO:33] and 2 [SEQ ID NO:34], 0.50 µM each HUMTPOX primers 1 [SEQ ID NO:35] and 2 [FL-SEQ ID NO:36], 0.20 µM each HUMTH01 primers 1 [SEQ ID NO:37] and 2 [FL-SEQ ID NO:38], 0.55 µM each HUMvWFA31 primers 1 [SEQ ID NO:39] and 2 [FL-SEQ ID NO:40].

Amplified products were separated by denaturing polyacrylamide gel electrophoresis on a 32 cm gel for 50 min. at 40 W and products were visualized by detection of the fluorescent signals using the FMBIOFluorImager™ (Hitachi Software Engineering, San Bruno, Calif.).

Figure 23:
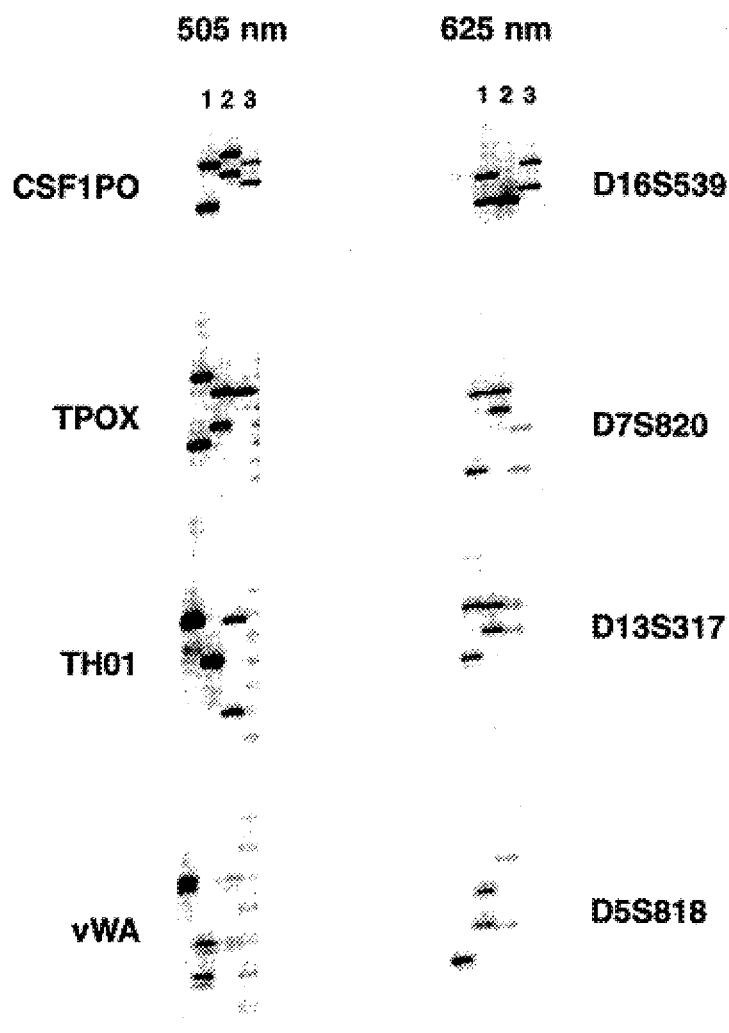
FIG. 23 is a laser-printed image showing the fluorescent detection of the products of simultaneous amplification of the loci D16S539, D7S820, D13S317, D5S818, HUMCSF1PO ("CSF1PO"), HUMTPOX ("TPOX"), HUMTH01 ("TH01") and HUMvWFA31 ("vWA") as detected with an FMBIO™ Fluorescent Scanner™ (Hitachi Software Engineering, San Bruno, Calif.) in Example 23.

Reference is made to FIG. 23 which displays the amplified fragments of each locus in separate 505 nm and 625 nm scans of the same gel revealing fluorescein-labeled and tetramethyl-rhodamine labeled material, respectively. Lanes 1 to 3 contain DNA samples simultaneously co-amplified for the loci D16S539, D7S820, D13S317, D5S818, HUMCSF1PO ("CSF1PO"), HUMTPOX ("TPOX"), HUMTH01 ("TH01") and HUMvWFA31 ("vWA").

Example 24

Fluorescent Detection of Multiplex Amplification of Loci D3S1539, D19S253, D13S317, and D20S481

In this example, a DNA template was amplified simultaneously at the individual loci D3S1539, D19S253, D13S317 and D20S481 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.75 µM each D3S1539 primers 1 [SEQ ID NO:7] and 2 [FL-SEQ ID NO:49], 0.75 µM each D19S253 primers 1 [FL-SEQ ID NO:50] and 2 [SEQ ID NO:51], 0.50 µM each D13S317 primers 1 [SEQ ID NO:3] and 2 [FL-SEQ ID NO:4], 0.50 µM each D20S481 primers 1 [SEQ ID NO:52] and 2 [FL-SEQ ID NO:53].

Amplified products were separated by denaturing polyacrylamide gel electrophoresis on a 32 cm gel for 50 min. at 40 W and products were visualized by detection of the fluorescent signals using the FluorImager™ fluorescent scanner (Molecular Dynamics, Sunnyvale, Calif.).

Figure 24:
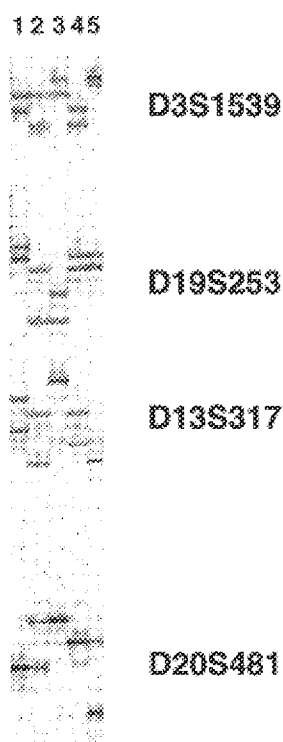
FIG. 24 is a laser-printed image showing the fluorescent detection of the products of simultaneous amplification of the loci D3S1539, D19S253, D13S317 and D20S481 as detected with a FluorImager™ fluorescent scanner (Molecular Dynamics, Sunnyvale, Calif.) in Example 24.

Reference is made to FIG. 24 which displays the amplified fragments of each locus. Lanes 1 to 5 contain DNA samples simultaneously co-amplified for the loci D3S1539, D19S253, D13S317 and D20S481.

Example 25

Fluorescent Detection of Multiplex Amplification of Loci D10S1239, D9S930, D4S2368, and D20S481

In this example, a DNA template was amplified simultaneously at the individual loci D10S1239, D9S930, D4S2368 and D20S481 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.30 µM each D10S1239 primers 1 [FL-SEQ ID NO:15] and 2 [SEQ ID NO:54], 0.40 µM each D9S930 primers 1 [SEQ ID NO:55] and 2 [FL-SEQ ID NO:14], 0.50 µM each D4S2368 primers 1 [SEQ ID NO:56] and 2 [FL-SEQ ID NO:57], 0.50 µM each D20S481 primers 1 [SEQ ID NO:52] and 2 [FL-SEQ ID NO:53].

Amplified products were separated by denaturing polyacrylamide gel electrophoresis on a 32 cm gel for 50 min. at 40 W and products were visualized by detection of the fluorescent signals using the FluorImager™ fluorescent scanner (Molecular Dynamics, Sunnyvale, Calif.).

Figure 25:
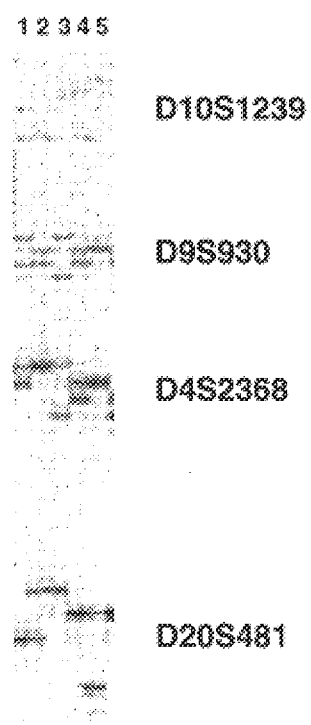
FIG. 25 is a laser-printed image showing the fluorescent detection of the products of simultaneous amplification of the loci D10S1239, D9S930, D4S2368 and D20S481 as detected with a FluorImager™ fluorescent scanner (Molecular Dynamics, Sunnyvale, Calif.) in Example 25.

Reference is made to FIG. 25 which displays the amplified fragments of each locus. Lanes 1 to 5 contain DNA samples simultaneously co-amplified for the loci D10S1239, D9S930, D4S2368 and D20S481.

Example 26

Silver Detection of Multiplex Amplification of Loci D16S539, D7S820 and D13S317

In this example, a DNA template was amplified simultaneously at the individual loci, D16S539, D7S820, and D13S317 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using 5 to 25 ng template, and 0.03 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 min.

Six amplification primers were used in combination, including 0.5 µM each D16S539 primers 1 [SEQ ID NO:29] and 2 [SEQ ID NO:58], 0.5 µM each D7S820 primers 1 [SEQ ID NO:1] and 2 [SEQ ID NO:2], 0.5 µM each D13S317 primers 1 [SEQ ID NO:3] and 2 [SEQ ID NO:4].

Amplified products were separated by denaturing polyacrylamide gel electrophoresis on a 32 cm gel for 50 min. at 40 W and products were visualized by silver stain analysis according to the protocol of Bassam et al.(1991).

Figure 26:
FIG. 26 is a photograph illustrating the silver stain detection of the products of simultaneous amplification of three loci, D16S539, D7S820, and D13S317, in Example 26.

Reference is made to FIG. 26 which displays the amplified fragments of each locus. Lanes 1 to 4 contain DNA samples simultaneously co-amplified for the loci D16S539, D7S820, and D13S317 and lane 5 displays a sample without DNA template subjected to the same procedures, i.e., a negative control.

Example 27

Silver Detection of Multiplex Amplification of Loci D16S539, D7S820, D13S317 and HUMvWFA31

In this example, a DNA template was amplified simultaneously at the individual loci, D16S539, D7S820, D13S317 and HUMvWFA31 in a single reaction vessel. The PCR amplification was performed in 25 µl of 1× STR Buffer (50 mM KCl, 10 mM Tris-HCl (pH 9.0 at 25° C.), 0.1% Triton X-100, 1. 5 mM $MgCl_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min, followed by 1 cycle of 60° C. for 30 min.

Eight amplification primers were used in combination, including 0.3 µM each D16S539 primers 1 [SEQ ID NO:29) and 2 [SEQ ID NO:30], 0.3 µM each D7S820 primers 1 [SEQ ID NO:13 and 2 [SEQ ID NO:2], 0.5 µM each D13S317 primers 1 [SEQ ID NO:3] and 2 (SEQ ID NO:4], 0.5 µM each HUMvWFA31 primers 1 [SEQ ID NO:59] and 2 [SEQ ID NO:60].

Amplified products were separated by denaturing polyacrylamide gel electrophoresis on a 32 cm gel for 50 min. at 40 W and products were visualized by silver stain analysis according to the protocol of Bassam et al.(1991).

Figure 27:
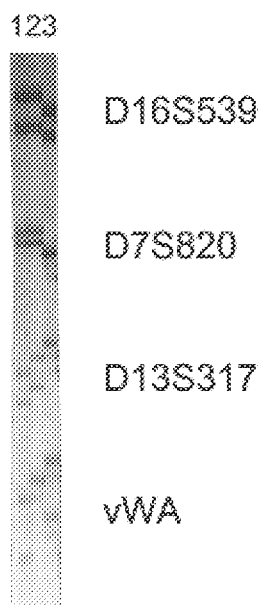
FIG. 27 is a photograph illustrating the silver stain detection of the products of simultaneous amplification of four loci, D16S539, D7S820, D13S317 and HUMvWFA31 ("vWA"), in Example 27.

Reference is made to FIG. 27 which displays the amplified fragments of each locus. Lanes 1 to 3 contain DNA samples simultaneously co-amplified for the loci D16S539, D7S820, D13S317 and HUMvWFA31 ("vWA").

Example 28

Silver Detection of Multiplex Amplification of Loci D10S1239, D9S930, and D13S317

In this example, a DNA template was amplified simultaneously at the individual loci, D10S1239, D9S930, and D13S317 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM $MgCl_2$ and 200 µM each of dATP, dCTP, dGTP and dTTP) using undetermined ng template, and 0.03 U Tag DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 minutes.

Six amplification primers were used in combination, including 1.0 µM each D10S1239 primers 1 [SEQ ID NO:15] and 2 [SEQ ID NO:54], 0.3 µM each D9S930 primers 1 [SEQ ID NO:55] and 2 [SEQ ID NO:61], 0.5 µM each D13S317 primers 1 [SEQ ID NO:3] and 2 [SEQ ID NO:4].

Amplified products were separated by denaturing polyacrylamide gel electrophoresis on a 40 cm gel for 60 min. at 60 W and products were visualized by silver stain analysis according to the protocol of Bassam et al.(1991).

Figure 28:
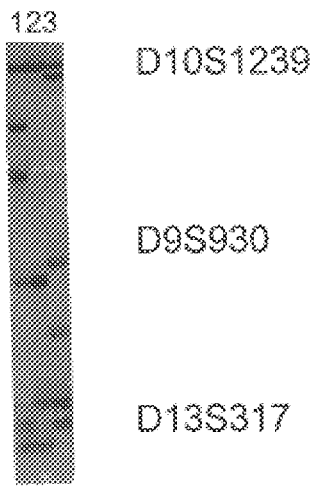
FIG. 28 is a photograph illustrating the silver stain detection of the products of simultaneous amplification of three loci, D10S1239, D9S930, and D13S317, in Example 28.

Reference is made to FIG. 28 which displays the amplified fragments of each locus. Lanes 1 to 3 contain DNA samples simultaneously co-amplified for the loci D10S1239, D9S930, and D13S317.

Example 29

Silver Detection of Multiplex Amplification of Loci D10S1239, D9S930, and D4S2368

In this example, a DNA template was amplified simultaneously at the individual loci, D10S1239, D9S930, and D4S2368 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using undetermined ng template, and 0.03 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Six amplification primers were used in combination, including 1.0 µM each D10S1239 primers 1 [SEQ ID NO:15] and 2 [SEQ ID NO:54], 0.3 µM each D9S930 primers 1 [SEQ ID NO:55] and 2 [SEQ ID NO:61], 0.15 µM each D4S2368 primers 1 (SEQ ID NO:56] and 2 [SEQ ID NO:57].

Amplified products were separated by denaturing polyacrylamide gel electrophoresis on a 40 cm gel for 60 min. at 60 W and products were visualized by silver stain analysis according to the protocol of Bassam et al.(1991).

Figure 29:
FIG. 29 is a photograph illustrating the silver stain detection of the products of simultaneous amplification of three loci, D10S1239, D9S930, and D4S2368, in Example 29.

Reference is made to FIG. 29 which displays the amplified fragments of each locus. Lanes 1 to 6 contain DNA samples simultaneously co-amplified for the loci D10S1239, D9S930, and D4S2368.

Example 30

Silver Detection of Multiplex Amplification of Loci D10S1239, D9S930, D4S2368 and D20S481

In this example, a DNA template was amplified simultaneously at the individual loci, D10S1239, D9S930, D4S2368 and D20S481 in a single reaction vessel. The PCR amplification was performed in 25 µl of 1× STR Buffer (50 mM KCl, 10 mM Tris-HCl (pH 9.0 at 25° C.), 0.1% Triton X-100, 1.55 mM MgCl$_2$ and 200 µM each of dATP, dCTP, dGTP and dTTP) using undetermined ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 1.0 µM each D10S1239 primers 1 [SEQ ID NO:15] and 2 [SEQ ID NO:54], 4.0 µM each D9S930 primers 1 [SEQ ID NO:55] and 2 [SEQ ID NO:14], 0.2 µM each D4S2368 primers 1 [SEQ ID NO:56] and 2 [SEQ ID NO:57] and 0.2 µM each D20S481 primers 1 [SEQ ID NO:52] and 2 [SEQ ID NO:53].

Amplified products were separated by denaturing polyacrylamide gel electrophoresis on a 40 cm gel for 67 min. at 60 W and products were visualized by silver stain analysis according to the protocol of Bassam et al.(1991).

Figure 30:
FIG. 30 is a photograph illustrating the silver stain detection of the products of simultaneous amplification of four loci, D10S1239, D9S930, D4S2368 and D20S481, in Example 30.

Reference is made to FIG. 30 which displays the amplified fragments of each locus. Lanes 1 to 4 contain DNA samples simultaneously co-amplified for the loci D10S1239, D9S930, D4S2368 and D20S481.

Example 31

Silver Detection of Multiplex Amplification of Loci D3S1539, D19S253 and D13S317

In this example, a DNA template was amplified simultaneously at the individual loci, D3S1539, D19S253 and D13S317 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 5.0 ng template, and 0.03 U Tag DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min.

Six amplification primers were used in combination, including 1.0 µM each D3S1539 primers 1 [SEQ ID NO:7] and 2 [SEQ ID NO:49], 1.0 µM each D19S253 primers 1 [SEQ ID NO:50] and 2 [SEQ ID NO:51], 0.5 µM each D13S317 primers 1 [SEQ ID NO:3] and 2 [SEQ ID NO:4].

Amplified products were separated by denaturing polyacrylamide gel electrophoresis on a 40 cm gel for 65 min. at 60 W and products were visualized by silver stain analysis according to the protocol of Bassam et al.(1991).

Figure 31:
FIG. 31 is a photograph illustrating the silver stain detection of the products of simultaneous amplification of three loci, D3S1539, D19S253 and D13S317, in Example 31.

Reference is made to FIG. 31 which displays the amplified fragments of each locus. Lanes 1 to 4 contain DNA samples simultaneously co-amplified for the loci D3S1539, D19S253 and D13S317 and lane 5 displays a sample without DNA template subjected to the same procedures, i.e., a negative control.

Example 32

Silver Detection of Multiplex Amplification of Loci D3S1539, D19S253, D4S2368 and D20S481

In this example, a DNA template was amplified simultaneously at the individual loci, D3S1539, D19S253, D4S2368 and D20S481 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 5 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min.

Eight amplification primers were used in combination, including 1.0 µM each D3S1539 primers 1 [SEQ ID NO:7] and 2 [SEQ ID NO:49], 0.5 µM each D19S253 primers 1 [SEQ ID NO:50] and 2 [SEQ ID NO:51], 0.1 µM each D4S2368 primers 1 [SEQ ID NO:56] and 2 [SEQ ID NO:57]], 0.1 µM each D20S481 primers 1 [SEQ ID NO:52] and 2 [SEQ ID NO:53].

Amplified products were separated by denaturing polyacrylamide gel electrophoresis on a 40 cm gel for 65 min. at 60 W and products were visualized by silver stain analysis according to the protocol of Bassam et al.(1991).

Figure 32:
FIG. 32 is a photograph illustrating the silver stain detection of the products of simultaneous amplification of four loci, D3S1539, D19S253, D4S2368 and D20S481, in Example 32.

Reference is made to FIG. 32 which displays the amplified fragments of each locus. Lanes 1 to 4 contain DNA samples simultaneously co-amplified for the loci D3S1539, D19S253, D4S2368 and D20S481 and lane 5 displays a sample without DNA template subjected to the same procedures, i.e., a negative control.

Example 33

Silver Detection of Multiplex Amplification of Loci D3S1539, D19S253, D13S317 and D20S481

In this example, a DNA template was amplified simultaneously at the individual loci, D3S1539, D19S253, D13S317 and D20S481 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 0.5 to 250 ng template, and 0.04 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Eight amplification primers were used in combination, including 0.5 µM each D3S1539 primers 1 [SEQ ID NO:7[ and 2 [SEQ ID NO:49], 0.5 µM each D19S253 primers 1 [SEQ ID NO:50[ and 2 (SEQ ID NO:51], 0.5 µM each D13S317 primers 1 (SEQ ID NO:3] and 2 [SEQ ID NO:4 ], 0.2 µM each D20S481 primers 1 [SEQ ID NO:52] and 2 [SEQ ID NO:53].

Amplified products were separated by denaturing polyacrylamide gel electrophoresis on a 40 cm gel for 68 min. at 60 W and products were visualized by silver stain analysis according to the protocol of Bassam et al.(1991).

Figure 33:
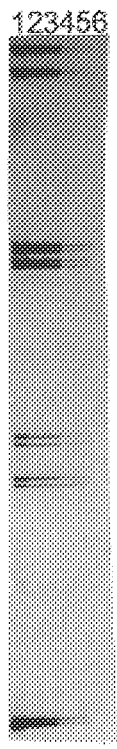
FIG. 33 is a photograph illustrating the silver stain detection of the products of simultaneous amplification of four loci, D3S1539, D19S253, D13S317 and D20S481, in Example 33.

Reference is made to FIG. 33 which displays the amplified fragments of each locus. Lanes 1 to 5 contain DNA samples simultaneously co-amplified for the loci D3S1539, D19S253, D13S317 and D20S481 and lane 6 displays a sample without DNA template subjected to the same procedures, i.e., a negative control.

Example 34

Silver Detection of Multiplex Amplification of Loci D10S1239, D9S930 and D20S481

In this example, a DNA template was amplified simultaneously at the individual loci, D10S1239, D9S930 and D20S481 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 0.5 to 250 ng template, and 0.03 U Taq DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Six amplification primers were used in combination, including 1.0 µM each D10S1239 primers 1 [SEQ ID NO:15] and 2 [SEQ ID NO:54], 4.0 µM each D9S930 primers 1 [SEQ ID NO:55] and 2 [SEQ ID NO:14], and 0.2 µM each D20S481 primers 1 [SEQ ID NO:52] and 2 [SEQ ID NO:53].

Amplified products were separated by denaturing polyacrylamide gel electrophoresis on a 40 cm gel for 68 min. at 60 W and products were visualized by silver stain analysis according to the protocol of Bassam et al.(1991).

Figure 34:
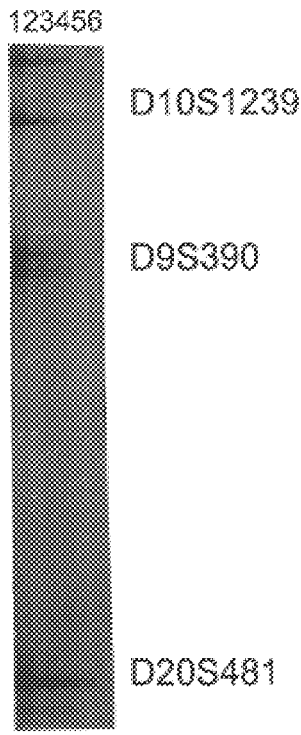
FIG. 34 is a photograph illustrating the silver stain detection of the products of simultaneous amplification of three loci, D10S1239, D9S930 and D20S481, in Example 34.

Reference is made to FIG. 34 which displays the amplified fragments of each locus. Lanes 1 to 5 contain DNA samples simultaneously co-amplified for the loci D10S1239, D9S930 and D20S481 and lane 6 displays a sample without DNA template subjected to the same procedures, i.e., a negative control.

Example 35

Silver Detection of Multiplex Amplification of Loci D10S1239, D4S2368 and D20S481

In this example, a DNA template was amplified simultaneously at the individual loci, D10S1239, D4S2368 and D20S481 in a single reaction vessel. The PCR amplification was performed in 25 µl of 1× STR Buffer (50 mM KCl, 10 mM Tris-HCl (pH 9.0 at 25° C.), 0.1% Triton X-100, 1.5 mM MgCl$_2$ and 200 µM each of dATP, dCTP, dGTP and dTTP) using 0.5 to 250 ng template, and 0.03 U Tag DNA Polymerase/µl. A Thermal Cycler 480 (Perkin Elmer, Foster City, Calif.) was employed with the following amplification protocol: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min., followed by 1 cycle of 60° C. for 30 min.

Six amplification primers were used in combination, including 1.0 µM each D10S1239 primers 1 [SEQ ID NO:15] and 2 [SEQ ID NO:54], 0.2 µM each D4S2368 primers 1 [SEQ ID NO:56] and 2 [SEQ ID NO:57], and 0.2 µM each D20S481 primers 1 [SEQ ID NO:52] and 2 [SEQ ID NO:53].

Amplified products were separated by denaturing polyacrylamide gel electrophoresis on a 40 cm gel for 68 min. at 60 W and products were visualized by silver stain analysis according to the protocol of Bassam et al.(1991).

Figure 35:
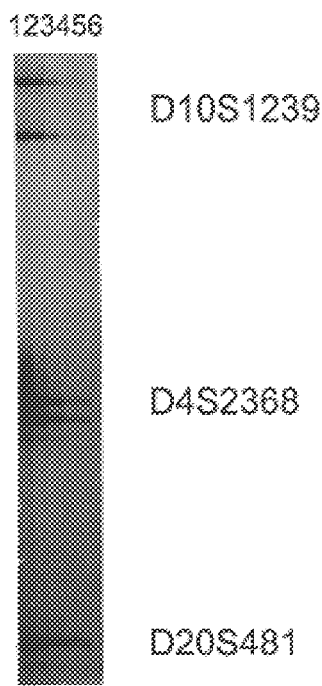
FIG. 35 is a photograph illustrating the silver stain detection of the products of simultaneous amplification of three loci, D10S1239, D4S2368 and D20S481, in Example 35.

Reference is made to FIG. 35 which displays the amplified fragments of each locus. Lanes 1 to 5 contain DNA samples simultaneously co-amplified for the loci D10S1239, D4S2368 and D20S481 and lane 6 displays a sample without DNA template subjected to the same procedures, i.e., a negative control.

What is claimed is:

1. A method of simultaneously determining the alleles present in at least four short tandem repeat loci from one or more DNA samples, comprising:

(a) obtaining at least one DNA sample to be analyzed, (b) selecting a set of at least four short tandem repeat loci of the DNA sample to be analyzed which can be amplified together, wherein the at least four loci in the set are selected from the group of loci consisting of: D3S1539, D4S2368, D5S818, D7S820, D9S930, D10S1239, D13S317, D14S118, D14S548, D14S562, D16S490, D16S539, D16S753, D17S1298, D17S1299, D19S253, D20S481, D22S683, HUMCSF1PO, HUMTPOX, HUMTH01, HUMF13A01, HUMBFXIII, HUMLIPOL, HUMvWFA31;

(c) co-amplifying the loci in the set in a multiplex amplification reaction, wherein the product of the reaction is a mixture of amplified alleles from each of the co-amplified loci in the set; and (d) evaluating the amplified alleles in the mixture to determine the alleles present at each of the loci analyzed in the set within the DNA sample.

2. The method of claim 1, wherein the set of at least four loci co-amplified therein is a set of four loci, wherein the set of four loci is selected from the group of sets of loci consisting of:

D3S1539, D7S820, D13S317, D5S818;
D17S1298, D7S820, D13S317, D5S818;
D20S481, D7S820, D13S317, D5S818;
D9S930, D7S820, D13S317, D5S818;
D10S1239, D7S820, D13S317, D5S818;
D14S118, D7S820, D13S317, D5S818;
D14S562, D7S820, D13S317, D5S818;
D14S548, D7S820, D13S317, D5S818;
D16S490, D7S820, D13S317, D5S818;
D17S1299, D7S820, D13S317, D5S818;
D16S539, D7S820, D13S317, D5S818;
D22S683, D7S820, D13S317, D5S818;
D16S753, D7S820, D13S317, D5S818;
D3S1539, D19S253, D13S317, D20S481;
D3S1539, D19S253, D4S2368, D20S481;
D10S1239, D9S930, D4S2368, D20S481; and
D16S539, D7S820, D13S317, HUMvWFA31.

3. The method of claim 1, wherein the set of at least four loci co-amplified therein is a set of six loci, wherein the set of six loci is selected from the group of sets of loci consisting of:

D16S539, D7S820, D13S317, D5S818, HUMCSF1PO, HUMTPOX; and
D16S539, D7S820, D13S317, D5S818, HUMF13A01, HUMFESFPS.

4. The method of claim 1, wherein the set of at least four loci co-amplified therein is a set of seven loci, wherein the set is selected from the group of sets of loci consisting of:

D16S539, D7S820, D13S317, D5S818, HUMCSF1PO, HUMTPOX, HUMTH01; and
D16S539, D7S820, D13S317, D5S818, HUMF13A01, HUMFESFPS, HUMBFXIII.

5. The method of claim 1, wherein the set of at least four loci co-amplified therein is a set of at least eight loci, and wherein the set is selected from the group of sets of loci consisting of:

D16S539, D7S820, D13S317, D5S818, HUMCSF1PO, HUMTPOX, HUMTH01, HUMvWFA31; and
D16S539, D7S820, D13S317, D5S818, HUMF13A01, HUMFESFPS, HUMBFXIII, HUMLIPOL.

6. The method of claim 1, wherein the multiplex amplification reaction is done using at least four pair of primers flanking the at least four loci analyzed.

7. The method of claim 6, additionally comprising the step of selecting pairs of primers for the multiplex amplification reaction which produce alleles from each locus that do not overlap the alleles of the other loci in the set co-amplified therein, when the alleles are separated by gel electrophoresis.

8. The method of claim 6, wherein at least one of each of the pairs of primers used in the multiplex amplification reaction has a sequence selected from one of the groups of sequences consisting of:

SEQ ID NO:1 and SEQ ID NO:2, when one of the loci in the set is D7S820;

SEQ ID NO:3 and SEQ ID NO:4, when one of the loci in the set is D13S317;
SEQ ID NO:5 and SEQ ID NO:6, when one of the loci in the set is D5S818;
SEQ ID NO:7, SEQ ID NO:8, and SEQ ID NO:49, when one of the loci in the set is D3S1539;
SEQ ID NO:9, SEQ ID NO:10, when one of the loci in the set is D17S1298;
SEQ ID NO:11, SEQ ID NO:12, SEQ ID NO:52, SEQ ID NO:53, when one of the loci in the set is D20S481;
SEQ ID NO:13, SEQ ID NO:14, SEQ ID NO:55, SEQ ID NO:61, when one of the loci in the set is D9S930;
SEQ ID NO:15, SEQ ID NO:16, SEQ ID NO:54, when one of the loci in the set is D10S1239;
SEQ ID NO:17, SEQ ID NO:18, when one of the loci in the set is D14S118;
SEQ ID NO:19, SEQ ID NO:20, when one of the loci in the set is D14S562;
SEQ ID NO:21, SEQ ID NO:22, when one of the loci in the set is D14S548;
SEQ ID NO:23, SEQ ID NO:24, when one of the loci in the set is D16S490;
SEQ ID NO:25, SEQ ID NO:26, when one of the loci in the set is D16S753;
SEQ ID NO:27, SEQ ID NO:28, when one of the loci in the set is D17S1299;
SEQ ID NO:29, SEQ ID NO:30, SEQ ID NO:58, when one of the loci in the set is D16S539;
SEQ ID NO:31, SEQ ID NO:32, when one of the loci in the set is D22S683;
SEQ ID NO:33, SEQ ID NO:34, when one of the loci in the set is HUMCSF1PO;
SEQ ID NO:35, SEQ ID NO:36, when one of the loci in the set is HUMTPOX;
SEQ ID NO:37, SEQ ID NO:38, when one of the loci in the set is HUMTH01;
SEQ ID NO:39, SEQ ID NO:40, SEQ ID NO:59, SEQ ID NO:60 when one of the loci in the set is HUMvWFA31;
SEQ ID NO:41, SEQ ID NO:42, when one of the loci in the set is HUMF13A01;
SEQ ID NO:43, SEQ ID NO:44, when one of the loci in the set is HUMFESFPS;
SEQ ID NO:45, SEQ ID NO:46, when one of the loci in the set is HUMBFXIII;
SEQ ID NO:47, SEQ ID NO:48, when one of the loci in the set is HUMLIPOL;
SEQ ID NO:50, SEQ ID NO:51, when one of the loci in the set is D19S253; and
SEQ ID NO:56, SEQ ID NO:57, when one of the loci in the set is D4S2368.

9. The method of claim 6, wherein the multiplex amplification reaction is a polymerase chain reaction.

10. The method of claim 1, wherein the amplified alleles are evaluated by comparing the amplified alleles to a size standard, wherein the size standard is selected from the group of size standards consisting of a DNA marker and a locus-specific allelic ladder.

11. The method of claim 1, wherein the amplified alleles are evaluated using polyacrylamide gel electrophoresis to separate the alleles, forming a polyacrylamide gel of separated alleles.

12. The method of claim 11, wherein the separated alleles in the polyacrylamide gel are determined by visualizing the alleles with silver stain analysis.

13. The method of claim 11, wherein primers capable of binding to a region flanking each of the loci in the set are used in co-amplifying the loci, wherein at least one of the primers used in co-amplifying each locus has a fluorescent label covalently attached thereto such that the amplified alleles produced therefrom are fluorescently labeled, and wherein the separated alleles in the polyacrylamide gel are determined by visualizing the alleles with fluorescent analysis.

14. The method of claim 13, wherein the fluorescent label is selected from the group of labels consisting of fluorescein and tetramethyl rhodamine.

15. The method of claim 1 wherein the at least one DNA sample to be analyzed is isolated from human tissue, wherein the human tissue is selected from the group of human tissue consisting of blood, semen, vaginal cells, hair, saliva, urine, amniotic fluid containing placental cells or fetal cells, and mixtures of any of the tissues listed above.

16. A method of simultaneously determining the alleles present in three short tandem repeat loci from one or more DNA samples, comprising:
  (a) obtaining at least one DNA sample to be analyzed,
  (b) selecting a set of three short tandem repeat loci of the DNA sample to be analyzed which can be amplified together, wherein the set of three loci is selected from the group of sets of loci consisting of:
  D3S1539, D19S253, D13S317;
  D10S1239, D9S930, D20S481;
  D10S1239, D4S2368, D20S481;
  D10S1239, D9S930, D4S2368;
  D16S539, D7S820, D13S317; and
  D10S1239, D9S930, D13S317.
  (c) co-amplifying the three loci in the set in a multiplex amplification reaction, wherein the product of the reaction is a mixture of amplified alleles from each of the co-amplified loci in the set; and
  (d) evaluating the amplified alleles in the mixture to determine the alleles present at each of the loci analyzed in the set within the DNA sample.

17. The method of claim 16, wherein the multiplex amplification reaction is done using three pair of primers, wherein each pair of primers flanks one of the three short tandem repeat loci in the set of loci co-amplified in the reaction.

18. The method of claim 17, wherein each of the three pair of primers used in the multiplex amplification reaction is designed to hybridize with an allele of a locus in the set of loci co-amplified in the reaction, wherein:
  when D7S820 is one of the loci in the set of loci co-amplified, at least one of the primers has a sequence selected from the group consisting of SEQ ID NO:1 and SEQ ID NO:2;
  when D13S317 is one of the loci in the set of loci co-amplified, at least one of the primers has a sequence selected from the group consisting of SEQ ID NO:3 and SEQ ID NO:4;
  when D20S481 is one of the loci in the set of loci co-amplified, at least one of the primers has a sequence selected from the group consisting of SEQ ID NO:11, SEQ ID NO:12, SEQ ID NO:52, SEQ ID NO:53;
  when D9S930 is one of the loci in the set of loci co-amplified, at least one of the primers has a sequence selected from the group consisting of SEQ ID NO:13, SEQ ID NO:14, SEQ ID NO:55 and SEQ ID NO:61;
  when D10S1239 is one of the loci in the set of loci co-amplified, at least one of the primers has a sequence selected from the group consisting of SEQ ID NO:15, SEQ ID NO:16 and SEQ ID NO:44;

when D16S539 is one of the loci in the set of loci co-amplified, at least one of the primers has a sequence selected from the group consisting of SEQ ID NO:29 and SEQ ID NO:30; and when D4S2368 is one of the loci in the set of loci co-amplified, at least one of the primers has a sequence selected from the group consisting of SEQ ID NO:56 and SEQ ID NO:57.

19. The method of claim 16, wherein the multiplex amplification reaction is a polymerase chain reaction.

20. The method of claim 16, wherein the amplified alleles are evaluated by comparing the amplified alleles to a size standard, wherein the size standard is selected from the group of size standards consisting of a DNA marker and a locus-specific allelic ladder.

21. The method of claim 16, wherein the amplified alleles are evaluated using polyacrylamide gel electrophoresis to separate the alleles, forming a polyacrylamide gel of separated alleles.

22. The method of claim 21, wherein the separated alleles in the polyacrylamide gel are determined by visualizing the alleles with silver stain analysis.

23. The method of claim 21, wherein the separated alleles in the polyacrylamide gel are determined by visualizing the alleles with fluorescence analysis.

24. The method of claim 16 wherein the at least one DNA sample to be analyzed is isolated from human tissue, wherein the human tissue is selected from the group of human tissue consisting of blood, semen, vaginal cells, hair, saliva, urine, bone, buccal sample, amniotic fluid containing placental cells or fetal cells, and mixtures of any of the tissues listed above.

25. A kit for simultaneously analyzing short tandem repeat sequences in at least three loci, comprising a container which has oligonucleotide primers for co-amplifying a set of at least three short tandem repeat loci, wherein the set of loci are selected from the sets of loci consisting of:

D3S1539, D19S253, D13S317;
D10S1239, D9S930, D20S481;
D10S1239, D4S2368, D20S481;
D10S1239, D9S930, D4S2368;
D16S539, D7S820, D13S317;
D10S1239, D9S930, D13S317;
D3S1539, D7S820, D13S317, D5S818;
D17S1298, D7S820, D13S317, D5S818;
D20S481, D7S820, D13S317, D5S818;
D9S930, D7S820, D13S317, D5S818;
D10S1239, D7S820, D13S317, D5S818;
D14S118, D7S820, D13S317, D5S818;
D14S562, D7S820, D13S317, D5S818;
D14S548, D7S820, D13S317, D5S818;
D16S490, D7S820, D13S317, D5S818;
D17S1299, D7S820, D13S317, D5S818;
D16S539, D7S820, D13S317, D5S818;
D22S683, D7S820, D13S317, D5S818;
D16S753, D7S820, D13S317, D5S818;
D3S1539, D19S253, D13S317, D20S481;
D3S1539, D19S253, D4S2368, D20S481;
D10S1239, D9S930, D4S2368, D20S481;
D16S539, D7S820, D13S317, HUMvWFA31;
D16S539, D7S820, D13S317, D5S818, HUMCSF1PO, HUMTPOX;
D16S539, D7S820, D13S317, D5S818, HUMF13A01, HUMFESFPS;
D16S539, D7S820, D13S317, D5S818, HUMCSF1PO, HUMTPOX, HUMTH01;
D16S539, D7S820, D13S317, D5S818, HUMF13A01, HUMFESFPS, HUMBFXIII;
D16S539, D7S820, D13S317, D5S818, HUMCSF1PO, HUMTPOX, HUMTH01, HUMvWFA31; and
D16S539, D7S820, D13S317, D5S818, HUMF13A01, HUMFESFPS, HUMBFXIII, HUMLIPOL.

26. The kit of claim 25, wherein each of the oligonucleotide primers is designed to hybridize with an allele of one of the three loci in the set of loci selected, wherein:

when D7S820 is one of the loci in the set, at least one of the primers has a sequence selected from the group consisting of SEQ ID NO:1 and SEQ ID NO:2;

when D13S317 is one of the loci in the set, at least one of the primers has a sequence selected from the group consisting of SEQ ID NO:3 and SEQ ID NO:4;

when D5S818, at least one of the primers has a sequence selected from the group consisting of SEQ ID NO:5 and SEQ ID NO:6;

when D3S153, at least one of the primers has a sequence selected from the group consisting of SEQ ID NO:7, SEQ ID NO:8 and SEQ ID NO:49;

when D17S1298, at least one of the primers has a sequence selected from the group consisting of SEQ ID NO:9 and SEQ ID NO:10;

when D20S481, at least one of the primers has a sequence selected from the group consisting of SEQ ID NO:11, SEQ ID NO:12, SEQ ID NO:52, SEQ ID NO:53;

when D9S930, at least one of the primers has a sequence selected from the group consisting of SEQ ID NO:13, SEQ ID NO:14, SEQ ID NO:55, SEQ ID NO:61;

when D10S1239, at least one of the primers has a sequence selected from the group consisting of SEQ ID NO:15, SEQ ID NO:16, SEQ ID NO:54;

when D14S118, at least one of the primers has a sequence selected from the group consisting of SEQ ID NO:17, SEQ ID NO:18;

when D14S562, at least one of the primers has a sequence selected from the group consisting of SEQ ID NO:19, SEQ ID NO:20;

when D14S548, at least one of the primers has a sequence selected from the group consisting of SEQ ID NO:21, SEQ ID NO:22;

when D16S490, at least one of the primers has a sequence selected from the group consisting of SEQ ID NO:23, SEQ ID NO:24;

when D16S753, at least one of the primers has a sequence selected from the group consisting of SEQ ID NO:25, SEQ ID NO:26;

when D17S1299, at least one of the primers has a sequence selected from the group consisting of SEQ ID NO:27, SEQ ID NO:28;

when D16S539, at least one of the primers has a sequence selected from the group consisting of SEQ ID NO:29, SEQ ID NO:30, SEQ ID NO:58;

when D22S683, at least one of the primers has a sequence selected from the group consisting of SEQ ID NO:31, SEQ ID NO:32;

when HUMCSF1PO, at least one of the primers has a sequence selected from the group consisting of SEQ ID NO:33, SEQ ID NO:34;

when HUMTPOX, at least one of the primers has a sequence selected from the group consisting of SEQ ID NO:35; SEQ ID NO:36;

when HUMTH01, at least one of the primers has a sequence selected from the group consisting of SEQ ID NO:37, SEQ ID NO:38;

when HUMvWFA31, at least one of the primers has a sequence selected from the group consisting of SEQ ID NO:39, SEQ ID NO:40, SEQ ID NO:60;

when HUMF13A01, at least one of the primers has a sequence selected from the group consisting of SEQ ID NO:41, SEQ ID NO:42;

when HUMFESFPS, at least one of the primers has a sequence selected from the group consisting of SEQ ID NO:43, SEQ ID NO:44;

when HUMBFXIII, at least one of the primers has a sequence selected from the group consisting of SEQ ID NO:45, SEQ ID NO:46;

when HUMLIPOL, at least one of the primers has a sequence selected from the group consisting of SEQ ID NO:47, SEQ ID NO:48;

when D19S253, at least one of the primers has a sequence selected from the group consisting of SEQ ID NO:50, SEQ ID NO:51; and when D4S2368, at least one of the primers has a sequence selected from the group consisting of SEQ ID NO:56, SEQ ID NO:57.

27. The kit of claim 25, further comprising a container having reagents for at least one multiplex amplification reaction.

28. The kit of claim 25, further comprising a container having an allelic ladder.

29. The kit of claim 28, wherein each rung of the allelic ladder and at least one oligonucleotide primer for each of the loci in the set each have a label covalently attached thereto.

30. The kit of claim 29, wherein the label is a fluorescent label.

31. The kit of claim 30, wherein at least one of the oligonucleotide primers has a different fluorescent label covalently attached thereto than some of the other primer pairs in the container.

32. A method of simultaneously determining the alleles present in at least four short tandem repeat loci from one or more DNA samples, comprising:

(a) obtaining at least one DNA sample to be analyzed, (b) selecting a set of at least four short tandem repeat loci of the DNA sample to be analyzed which can be amplified together, wherein three of the loci in the set are D7S820, D13S317, and D5S818;

(c) co-amplifying the loci in the set in a multiplex amplification reaction, wherein the product of the reaction is a mixture of amplified alleles from each of the co-amplified loci in the set; and (d) evaluating the amplified alleles in the mixture to determine the alleles present at each of the loci analyzed in the set within the DNA sample.

33. The method of claim 32, wherein the multiplex amplification reaction is done using at least four pair of primers flanking the at least four loci analyzed.

34. The method of claim 33, additionally comprising the step of selecting pairs of primers for the multiplex amplification reaction which produce alleles from each locus that do not overlap the alleles of the other loci in the set co-amplified therein, when the alleles are separated by gel electrophoresis.

35. The method of claim 32, wherein the multiplex amplification reaction is a polymerase chain reaction.

36. The method of claim 32, wherein the amplified alleles are evaluated by comparing the amplified alleles to a size standard, wherein the size standard is selected from the group of size standards consisting of a DNA marker and a locus-specific allelic ladder.

37. The method of claim 32, wherein the amplified alleles are evaluated using polyacrylamide gel electrophoresis to separate the alleles, forming a polyacrylamide gel of separated alleles.

38. The method of claim 37, wherein the separated alleles in the polyacrylamide gel are determined by visualizing the alleles with silver stain analysis.

39. The method of claim 37, wherein primers capable of binding to a region flanking each of the loci in the set are used in co-amplifying the loci, wherein at least one of the primers used in co-amplifying each locus has a fluorescent label covalently attached thereto such that the amplified alleles produced therefrom are fluorescently labeled, and wherein the separated alleles in the polyacrylamide gel are determined by visualizing the alleles with fluorescence analysis.

40. The method of claim 39, wherein the fluorescent label is selected from the group of labels consisting of fluorescein and tetramethyl rhodamine.

41. The method of claim 6, wherein one of each of at the least four pair of primers used in the multiplex amplification reaction has a fluorescent label covalently attached thereto.

42. The method of claim 41, wherein at least four of the primers used in the multiplex amplification reaction have the same fluorescent label covalently attached thereto.

43. The kit of claim 30, wherein at least four of the oligonucleotide primers have the same fluorescent label covalently attached thereto.

* * * * *